(12) United States Patent
Wingeier et al.

(10) Patent No.: US 11,364,383 B2
(45) Date of Patent: Jun. 21, 2022

(54) SYSTEM AND METHOD FOR ELECTRICALLY STIMULATING A USER

(71) Applicant: Halo Neuro, Inc., San Francisco, CA (US)

(72) Inventors: Brett Wingeier, San Francisco, CA (US); Rob Helvestine, San Francisco, CA (US); Anne Swanberg, San Francisco, CA (US); Daniel Chao, San Francisco, CA (US)

(73) Assignee: Halo Neuro, Inc., San Francisco, CA (US)

( * ) Notice: Subject to any disclaimer, the term of this patent is extended or adjusted under 35 U.S.C. 154(b) by 203 days.

(21) Appl. No.: 16/653,478

(22) Filed: Oct. 15, 2019

(65) Prior Publication Data

US 2020/0215326 A1 Jul. 9, 2020

Related U.S. Application Data

(60) Provisional application No. 62/789,123, filed on Jan. 7, 2019.

(51) Int. Cl.
| | |
|---|---|
| *A61N 1/04* | (2006.01) |
| *A61N 1/05* | (2006.01) |
| *A61N 1/36* | (2006.01) |
| *H04W 4/80* | (2018.01) |
| *H04W 4/38* | (2018.01) |
| *H04W 88/02* | (2009.01) |

(52) U.S. Cl.
CPC ....... *A61N 1/36034* (2017.08); *A61N 1/0476* (2013.01); *A61N 1/0484* (2013.01); *H04W 4/38* (2018.02); *H04W 4/80* (2018.02); *H04W 88/02* (2013.01)

(58) Field of Classification Search
CPC .............. A61N 1/36034; A61N 1/0484; A61N 1/0476; A61N 1/36025; A61N 1/0472; A61N 1/0526; A61N 1/3603; H04W 4/80; H04W 4/38; H04W 88/02
See application file for complete search history.

(56) References Cited

U.S. PATENT DOCUMENTS

2017/0076414 A1* 3/2017 Egnal ................. G06Q 30/0635
2017/0182285 A1* 6/2017 Tyler .................... A61B 5/4806

* cited by examiner

*Primary Examiner* — Carl H Layno
*Assistant Examiner* — Anh-Khoa N Dinh
(74) *Attorney, Agent, or Firm* — Jeffrey Schox; Caitlin Ploch

(57) ABSTRACT

A system for electrically stimulating a user includes an electrode assembly, a control module, an electrode usage module, a communication module, a stimulus generator, and a client application. Additionally or alternatively, the system 100 can include any or all of: a head apparatus, a power source, a sensor subsystem, an electrical coupling subsystem, a user device, and/or any other suitable component(s). A method for electrically stimulating a user includes reading a tag of the electrode assembly, applying electrical stimulation to a user, determining and/or updating an electrode usage, and triggering an action based on the tag. Additionally or alternatively, the method can include any or all of: coupling an electrode assembly with a head apparatus, receiving an input from a user to initiate an electrical stimulation session, transmitting tag information, updating the tag, applying electrical stimulation to a user, verifying tag information, and/or any other suitable process(es).

6 Claims, 13 Drawing Sheets

Client application in a state where tag is not detected

Client application showing a specific stimulation (e.g., vertical jump) based on the specific primer band (e.g., fitness) detected Client application showing a specific stimulation (e.g., advanced guitar chords) based on the specific primer band (e.g., music) detected

SYSTEM AND METHOD FOR ELECTRICALLY STIMULATING A USER

CROSS-REFERENCE TO RELATED APPLICATIONS

This application claims the benefit of U.S. Provisional Application Ser. No. 62/789,123 filed 7 Jan. 2019, which is incorporated in its entirety herein by this reference.

TECHNICAL FIELD

This invention relates generally to the biosignals field, and more specifically to a new and useful system and method for electrically stimulating a user.

BACKGROUND

Electrode systems in the biosignals field are used to transmit electrical signals to a subject, and can be used to detect or measure biosignals from the subject. The quality and safety of the provided electrical stimulation is highly dependent on the state of the electrodes used. In electrode systems including modular electrodes (e.g., reusable, disposable, etc.), it can be difficult for a user to know when a new set of electrodes is required, since many factors can contribute to a degradation in stimulation quality of the electrodes; it is important to determine this, however, since overusing a set of electrodes can not only be ineffective, but potentially dangerous to a user.

Thus, there is a need in the biosignals field for a new and useful electrode usage tracking system and method. This invention provides such a new and useful system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1:
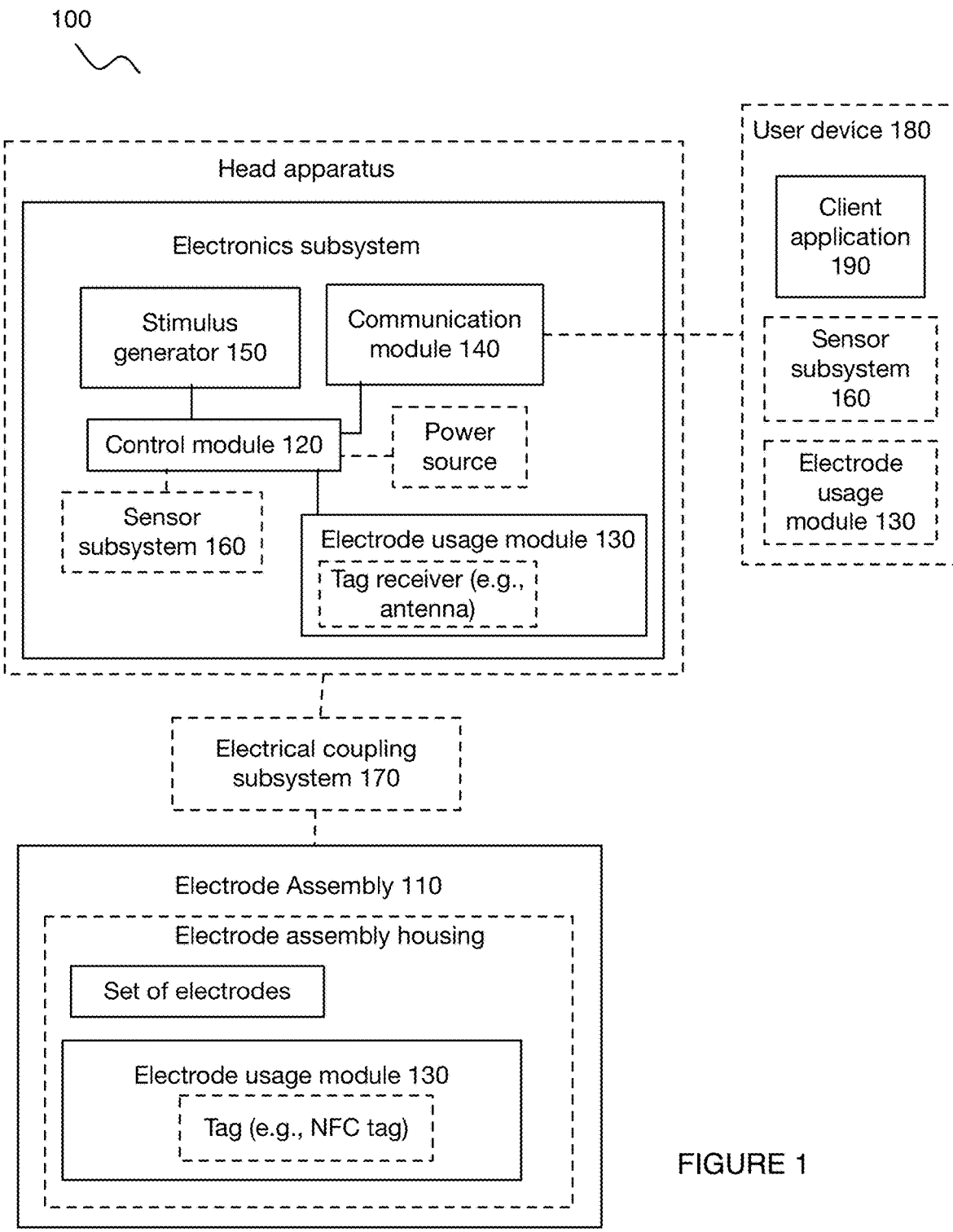
FIG. 1 depicts a schematic of a system for electrically stimulating a user.

As shown in FIG. 1, a system 100 for electrically stimulating a user includes an electrode assembly 110, a control module 120, an electrode usage module 130, a communication module 140, a stimulus generator 150, and a client application 190. Additionally or alternatively, the system 100 can include any or all of: a head apparatus, a power source, a sensor subsystem 160, an electrical coupling subsystem 170, a user device 180, and/or any other suitable component(s). Further additionally or alternatively, the system 100 can include any or all of the system components described in any or all of: U.S. patent application Ser. No. 14/470,683, filed 27 Aug. 2014, now issued as U.S. Pat. No. 9,889,290, U.S. patent application Ser. No. 14/878,647, filed 8 Oct. 2015, now issued as U.S. Pat. No. 9,486,618, U.S. patent application Ser. No. 15/335,240, filed 26 Oct. 2016, now issued as U.S. Pat. No. 10,315,026, U.S. patent application Ser. No. 15/916,170, filed 8 Mar. 2018, any of the Patent Applications and/or Issued Patents described below, each of which is incorporated in its entirety by this reference.

Figure 2:
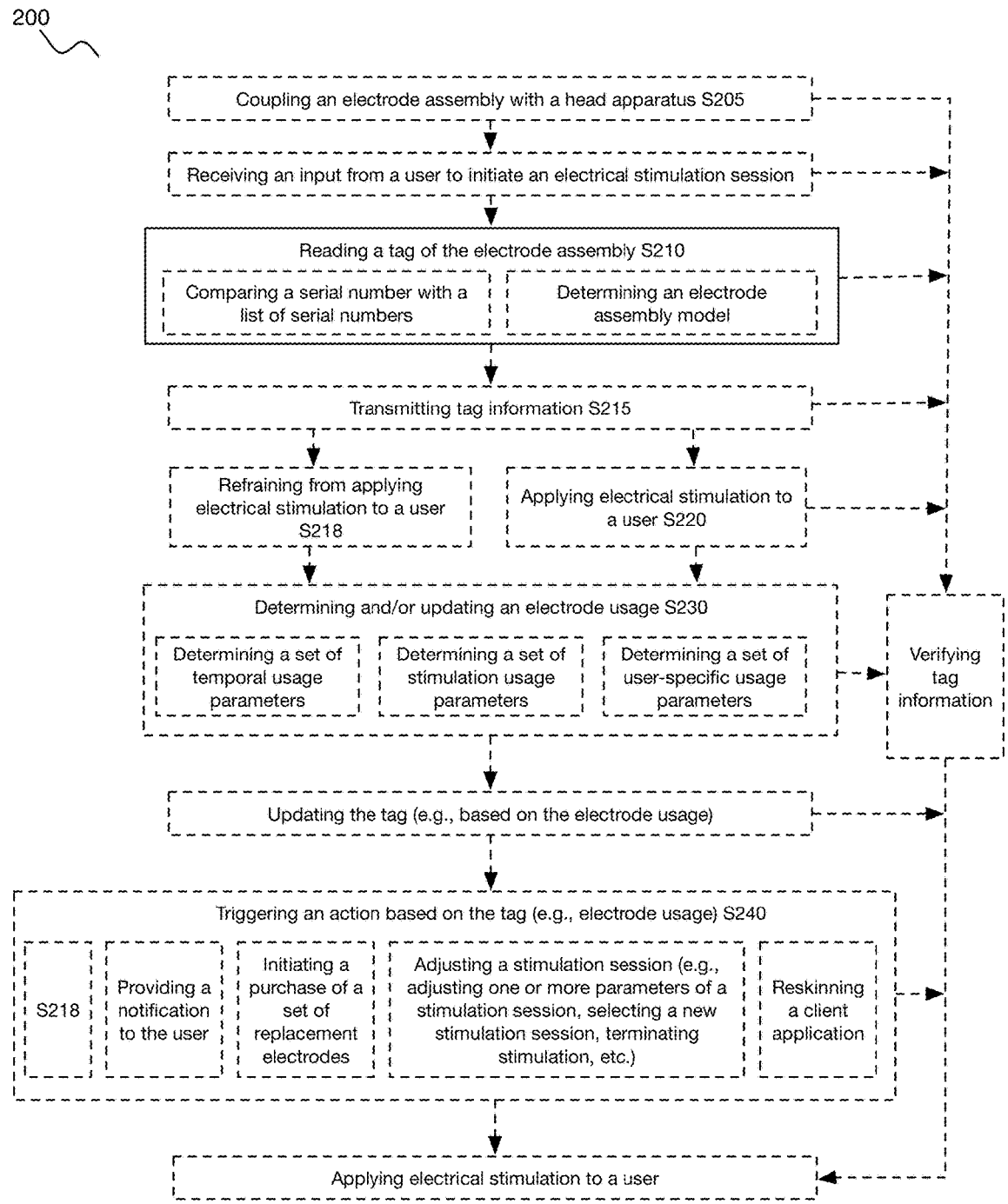
FIG. 2 depicts a schematic of a method for electrically stimulating a user.
Figure 3A:
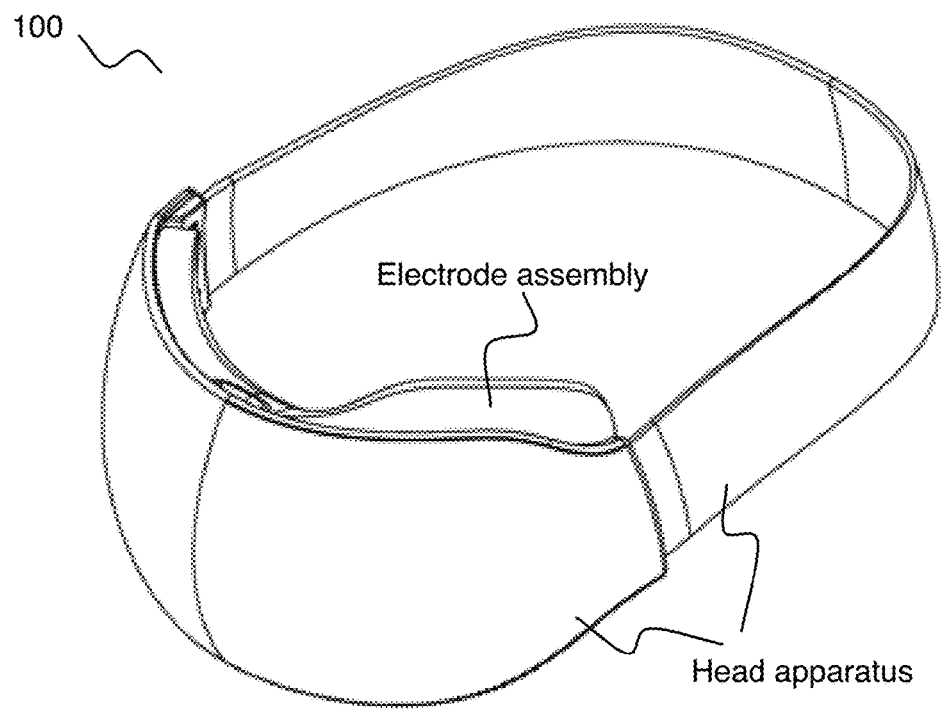
FIGS. 3A-3H depict a variation of the system.
Figure 3B:
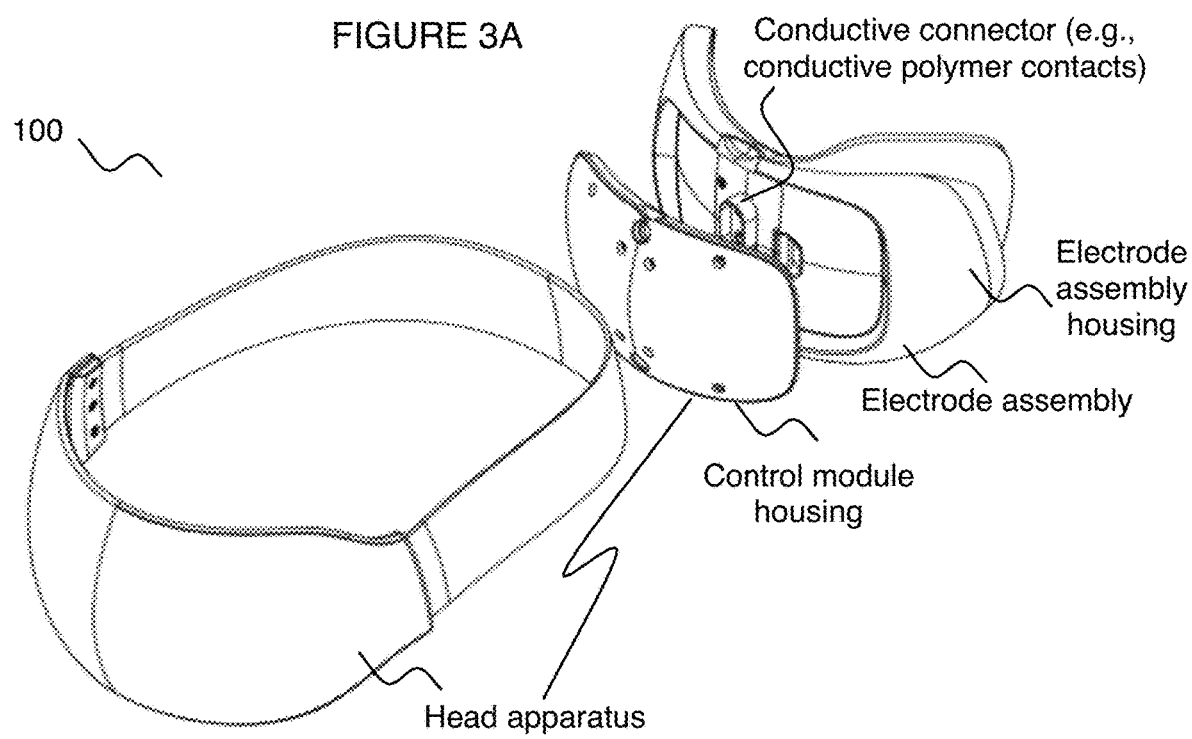
Figure 3C:
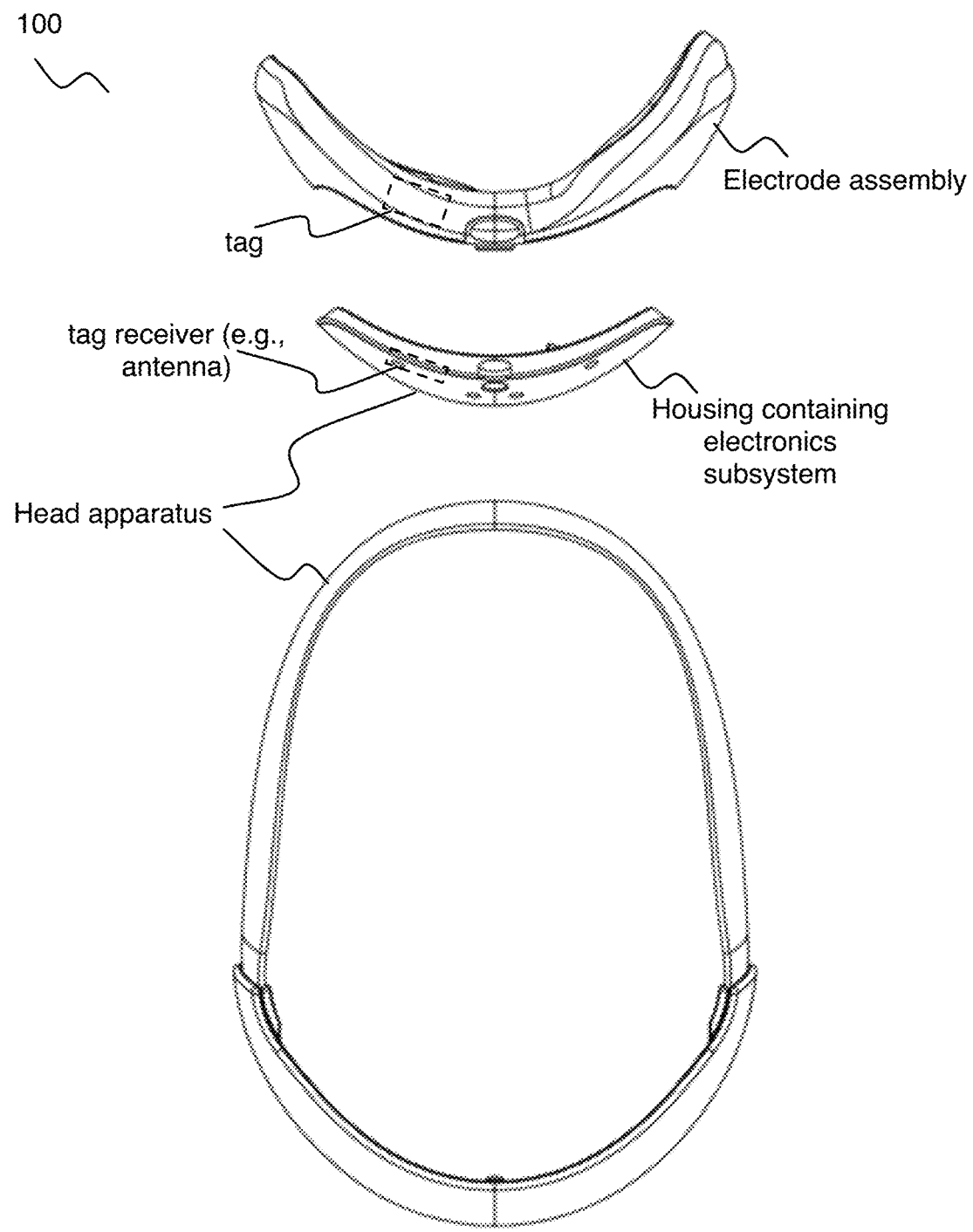
Figure 3D:
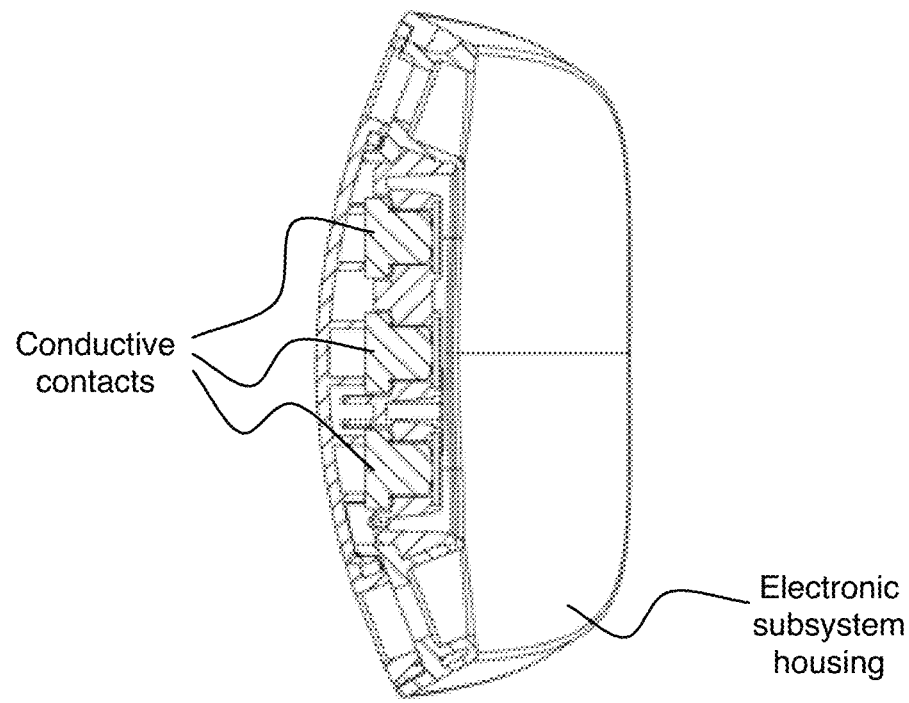
Figure 3E:
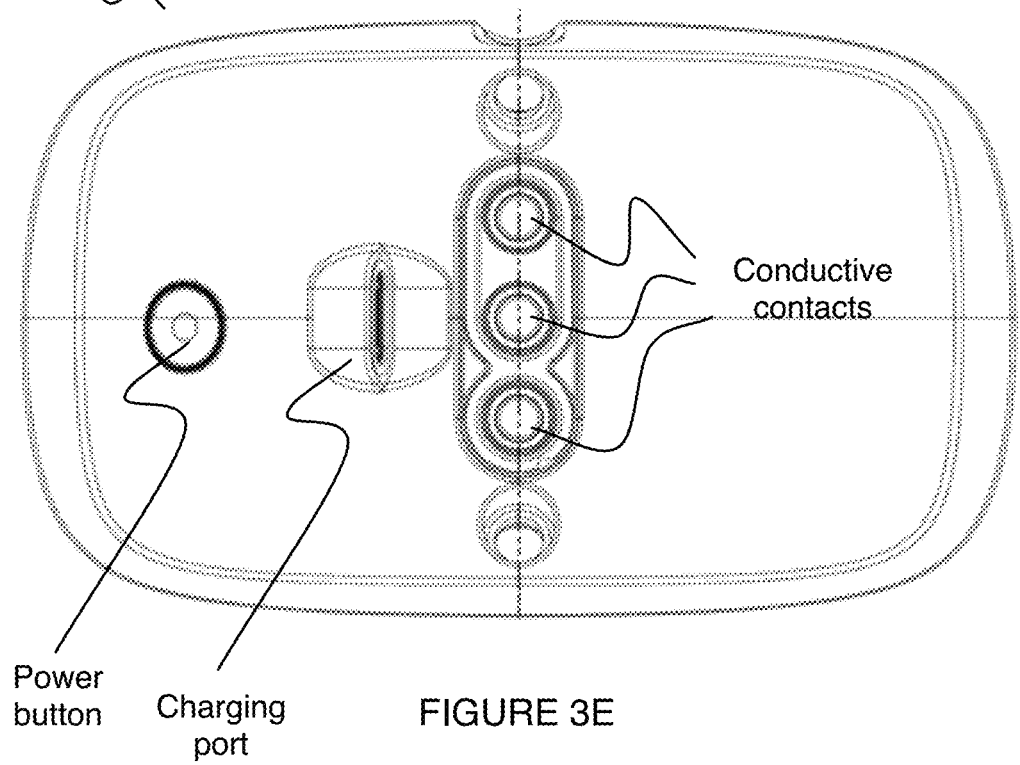
Figure 3F:
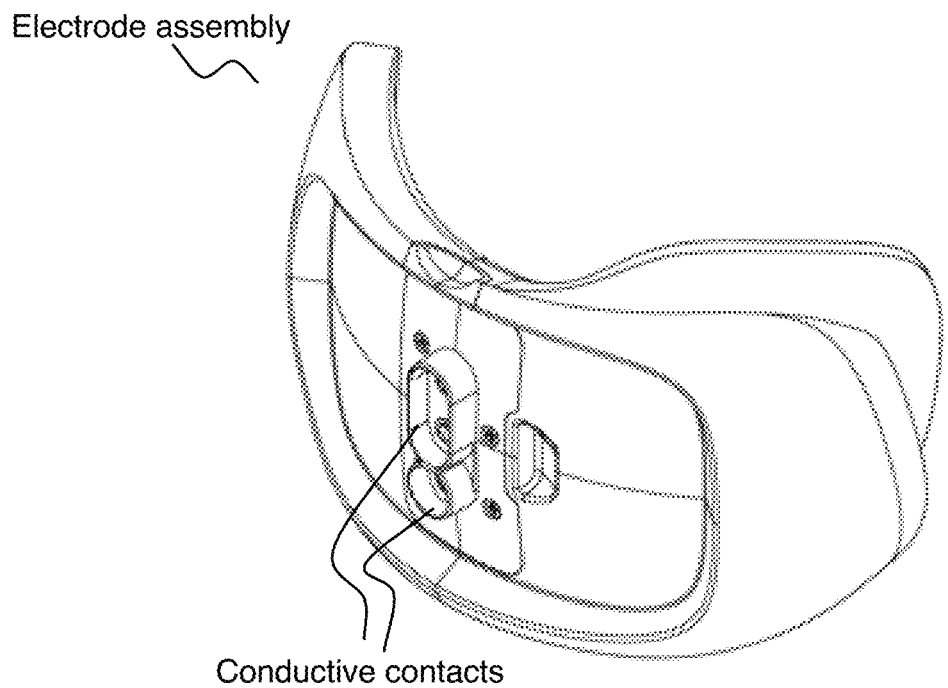
Figure 3G:
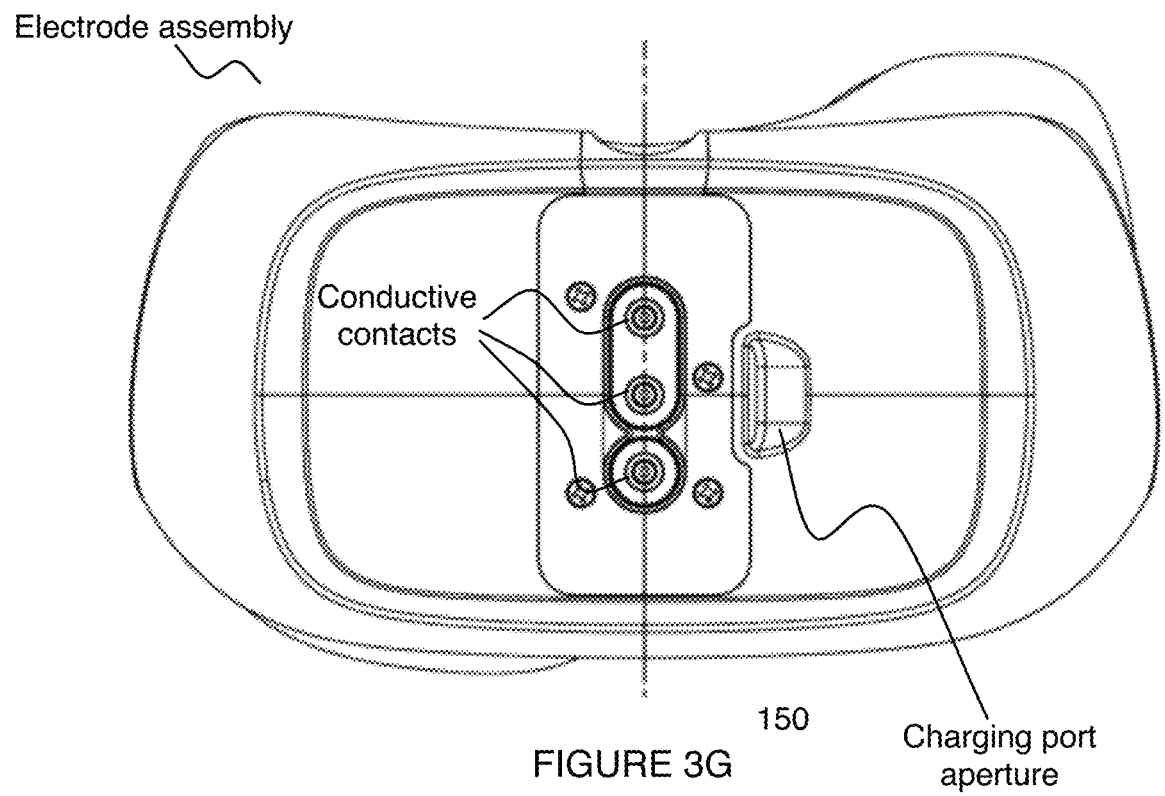
Figure 3H:
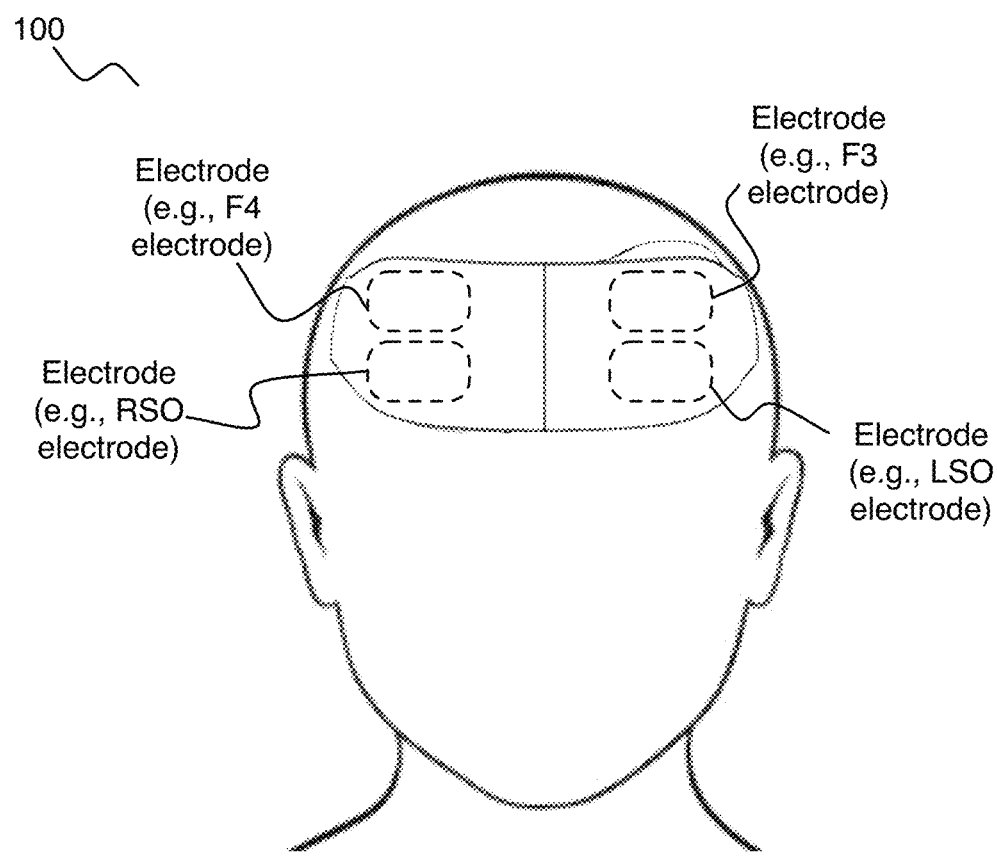

As shown in FIG. 2, a method 200 for electrically stimulating a user includes: reading a tag of the electrode assembly S210. Additionally, the method 200 can include any or all of: determining and/or updating an electrode usage S230; and triggering an action based on the tag S240; applying electrical stimulation to a user S220; refraining from applying electrical stimulation to a user S218; coupling an electrode assembly with a head apparatus S205; receiving an input from a user to initiate an electrical stimulation session; transmitting tag information S215; updating the tag; verifying tag information; and/or any other suitable process(es). Further additionally or alternatively, the method 200 can include any or all of the processes described in any or all of: U.S. patent application Ser. No. 14/470,747, filed 27 Aug. 2014, now issued as U.S. Pat. No. 9,630,005, U.S. application Ser. No. 15/426,212, now issued as U.S. Pat. No. 10,315,033, U.S. patent application Ser. No. 15/059,095, now issued as U.S. Pat. No. 9,782,585, U.S. patent application Ser. No. 16/195,728, filed 19 Nov. 2018, and any of the Patent Applications and/or Issued Patents described above, each of which is incorporated in its entirety by this reference.

2. Benefits

The system and/or method can confer several benefits over conventional systems and methods.

First, in some variations, the system and/or method confers the benefit of tracking usage of reusable electrodes used for electrically stimulating a user. In a specific example, the system and/or method confers the benefit of preventing ineffective stimulation sessions resulting from the user continuing to use electrodes that no longer perform to an acceptable degree.

Second, in some variations, the system and/or method confers the benefit of enabling stimulation to be safely applied to the user. In a specific example, the system and/or method confers the benefit of automatically adjusting or stopping stimulation if improper contact between the electrode and the user is detected.

Third, in some variations, the system and/or method confers the benefit of ensuring that a user has an adequate supply of reusable electrodes. In a specific example, an automated reminder and/or a refill order of electrodes is automatically placed based on electrode usage data.

Fourth, in some variations, the system and/or method confers the benefit of ensuring that a user is provided with an appropriate amount of stimulation. In a specific example, a prescribed amount of stimulation chosen to optimize safety and/or effectiveness consists of a prescribed number of uses and this prescribed number of uses is allowed to the user by furnishing the user (e.g., upon purchase of the device, upon a refill of the electrodes, upon an automatically triggered refill of the electrodes, etc.) with a set of electrodes that enables only this number of uses.

Additionally or alternatively, the system and/or method can confer any other suitable benefit(s).

3. System 100

The system 100 functions to apply stimulation to a user through a set of electrode units. Additionally, the system 100 can function to: monitor the use and the usage of the set of electrode units, such that stimulation is properly (e.g., effectively, safely, etc.) applied to the user; properly position (e.g., prevent slipping or movement, contour a user, etc.) one or more electrode units at the head of the user; facilitate sensing (e.g., biometric sensing) of signals from a user in cooperation with, or in the absence of, stimulation; and/or perform any other suitable function(s).

The system 100 is preferably configured to be worn by a user who is away from a research or clinical setting, such that the user can wear the system 100 while he or she is in a natural setting (e.g., at home, at a gym, outdoors, etc.). The system 100 can additionally or alternatively be configured to be operated by a user who is in a research setting, a clinical setting, or any other suitable setting. Furthermore, while some embodiments of the system are configured to be worn at the head of the user, alternative embodiments of the system 100 can be configured to be worn or coupled to any other suitable body region of the user.

3.1 System: Electrode Assembly 110

The system 100 includes an electrode assembly 110, which functions to apply electrical stimulation to the user (e.g., according to a particular stimulation pattern).

As such, in embodiments and variations, the system 100 and/or method(s) can be configured for application of one or more of: transcranial electrical stimulation (TES) in the form of transcranial direct current stimulation (tDCS), transcranial alternating current stimulation (tACS), transcranial magnetic stimulation (TMS), transcranial random noise stimulation (tRNS) (e.g., band-limited random noise stimulation), transcranial pulsatile stimulation (tPS), transcranial variable frequency stimulation (tVFS), band-limited stimulation transformed to increase RMS power while minimizing transients and clipping, and any other suitable form of TES. Furthermore, in any of the above examples and variations, the system 100 and/or method can be configured for delivery of stimulation as anodal stimulation and/or cathodal stimulation. In other examples, the electrical stimulation can additionally or alternatively comprise any other form of electrical stimulation (e.g., electrical muscle stimulation, etc.) configured to stimulate any other suitable region of the user's body, with any suitable penetration depth, and/or any suitable tissue structure (e.g., neural, musculoskeletal).

The electrode assembly includes a set of electrode units (equivalently referred to herein as electrodes), wherein the electrical stimulation is provided through the set of electrode units. The electrode units are preferably placed at a head region of the user, further preferably at a skin surface (e.g., forehead, scalp, scalp and hair, etc.) of a head region of the user. The electrode units can be configured to be positioned (e.g., during an operation mode wherein the system is applying electrical stimulation) at any or all of: a motor cortex region of the user, a frontal and/or prefrontal cortex region of the user (e.g., dorsolateral prefrontal cortex, F3 brain region, F4 brain region, a supraorbital brain region, forehead, etc.), and/or any other suitable head or other body region of the user.

The electrode units can include any suitable material(s) configured to establish an electrical connection (e.g., create an electrical pathway) with the user. The electrode units are preferably at least partially conformable and/or flexible, such that the electrode units can be comfortably worn by the user (e.g., during a normal task, while concentrating, while exercising, while sleeping, etc.). Additionally or alternatively, the electrode units can include any number of rigid materials. The electrode units can include, for instance, any or all of: a pad (e.g., conformable pad), sponge, fabric, polymer (e.g., conductive rubber, carbon rubber, etc.), metal, and/or any other suitable material(s). The electrode units can additionally or alternatively include any number of conductive particles (e.g., electrolytes, salt, etc.), liquids, gels, and/or any other materials embedded in, coated on, integrated with, sprayed on, soaked with, and/or otherwise coupled to the electrode units, wherein the conductive material(s) function to enable and/or enhance an electrical connection with the user.

In some variations, each electrode unit defines a set of protrusions (e.g., supporting a set of permeable bodies), such as any or all of the electrodes described in U.S. patent application Ser. No. 14/470,683, filed 27 Aug. 2014, now issued as U.S. Pat. No. 9,889,290, U.S. patent application Ser. No. 14/878,647, filed 8 Oct. 2015, now issued as U.S. Pat. No. 9,486,618, U.S. patent application Ser. No. 15/335,240, filed 26 Oct. 2016, now issued as U.S. Pat. No. 10,315,026, U.S. patent application Ser. No. 15/916,170, filed 8 Mar. 2018, each of which is incorporated herein in its entirety by this reference. In some variations, each electrode unit includes a layered structure (e.g., with hydrophilic layers, with hydrophobic layers, with conductive layers, with insulative layers, etc.), such as those described in U.S. Pat. No. 10,315,026.

In some variations, robust connection with the user provided by the elements (e.g., mechanical aspects) of the system 100 additionally or alternatively apply to transmission of non-electrical modes of stimulation according to other suitable methods. As such, the system 100 and/or method(s) can additionally or alternatively be configured to transmit non-electrical modes of stimulation (e.g., ultrasound stimulation, optical stimulation) by using any appropriate transducer or set of transducers in place of or in addition to electrode contacts. For instance, one variation of the system 100 can be used to provide ultrasound transducing elements at a desired body region of the user, as facilitated by an array of protrusions configured to displace obstacles to ultrasound stimulation at the body region of the user. In this variation, ultrasound transducing elements can be configured at any suitable position along a length of a protrusion and/or at a distal end of a protrusion. Other variations can, however, be configured to incorporate any other element(s) for stimulating the user.

The electrode assembly is preferably modular, such that the electrode assembly is partially or fully removable (e.g., removably couplable) from any or all of a remainder of the system, such as from a headset apparatus. This functions to enable easy replacement of the electrode assembly without requiring replacement of other components, such as the headset apparatus. This can add the complexity, however, of properly and accurately tracking usage of electrodes where a control module and/or a communication module are arranged (e.g., completely arranged) in a headset apparatus. The modular electrode assembly is preferably configured to be used for multiple uses (e.g., not single-use) and then replaced as determined by the method 200. Alternatively, the modular electrode assembly can be configured for a single use, permanent use, and/or any other suitable use case.

The electrode assembly preferably connects to the head apparatus through an electrical and a mechanical connector (e.g., single connector made from a conductive material, multiple connectors, mechanical connector with electrical contacts, etc.), such as one or more connectors described in U.S. patent application Ser. No. 15/627,717, filed 20 Jun.

2017, and/or any of the references described above, each of which is incorporated herein in its entirety by this reference.

The electrode assembly can optionally include one or more electrode support housings, which can function to enable coupling of the electrode assembly to a headset apparatus, protect the portion of the usage module (e.g., tag, NFC tag, etc.) and/or any other suitable component(s) (e.g., electrical coupler, conductive frame, tag, etc.) arranged at the electrode assembly of the system (e.g., from fluid ingress, from wear and tear, etc.). As such, the electrode housing preferably includes and/or defines at least a portion of one or more connectors as described above, wherein the complementary portion is arranged on the head apparatus. Additionally or alternatively, the electrode housing can include and/or define any other suitable components. The electrode housing is preferably replaced with the electrodes, but alternatively, the electrodes can be replaced with respect to the electrode housing. The electrode housing is preferably constructed from an insulative material but can additionally or alternatively include one or more conductive materials. The electrode housing is preferably rigid but can additionally or alternatively be semi-rigid, flexible, conformable, and/or otherwise configured.

In preferred variations, the system includes a single electrode housing configured to mechanically support each of the set of electrodes (e.g., at predetermined locations, at predetermined distances from each other, such that the electrodes stimulate the appropriate head regions of the user, etc.). Additionally or alternatively, each of the electrodes can have its own housing, support of the electrodes can include movable and adjustable positioning of the electrodes, and/or the electrodes can be otherwise supported.

3.2 System: Control Module 120

The system 100 includes an electronics subsystem including a control module 120 (e.g., controller, processor, etc.), which functions to apply an electrical stimulus (e.g., through a stimulus generator) to a user through one or more electrodes. Additionally or alternatively, the control module can function to store electrical stimulus patterns, share electrical stimulus patterns (e.g., between users through an application on a user device, the cloud, etc.), monitor device performance, implement a fail-safe (e.g., power shut-off in the event of overheating or stimulus parameter above a predetermined threshold, alarm, etc.), monitor and/or measure neural activity of a user, store and/or share neural activity recordings, or perform any other suitable function.

The control module is preferably electrically connected to the electrode assembly (e.g., through a conductive polymer backing of an electrode, through a set of permeable bodies, etc.), but can additionally or alternatively be in wireless communication with the electrode assembly and/or any other element in the system 100. In one example, for instance, a stimulus generator/deliverer onboard the system 100 can be controlled (e.g., wirelessly) from a remote source, such as a processor in a user device or a remote server system. An onboard control module is preferably connected (mechanically and/or electrically) to an electronics base (e.g., PCB) but can otherwise be arranged anywhere else in the system. In variations having an onboard control module, the onboard control module can be wirelessly coupled to a control module of an external device, such as a user device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi transceiver(s), Bluetooth transceiver(s), cellular transceiver(s), etc.), or any other suitable component.

In some variations, the processing system is distributed among a control module of the head apparatus and a processing subsystem of a user device.

The control module preferably includes one or more of: a controller (e.g., a microcontroller), processor (e.g., a microprocessor), system on a chip (SoC) or other integrated circuit, timing subsystem including a set of timers, and/or stimulus generator (e.g., multi-channel stimulus generator, set of stimulation control instructions, etc.), but can additionally or alternatively include any other circuitry, electronic component, or control unit configured to apply an electrical stimulus to a user.

The control module can include data storage (e.g., to store stimulation patterns), which can be onboard the system 100 (e.g., in the form of a memory chip, memory card, etc.) or external to the system 100 (e.g., via wireless communication with a remote server, the cloud, etc.).

The control module can also include a sensor system mounted to or integrated within any part of the system 100 (e.g., attached to the electrode housing 120, attached to the electronics housing, etc.). The system 100 can, for instance, include any one or more of: a moisture sensor, pressure sensor, contact sensor, optical sensor (e.g., light sensor, camera, etc.), orientation sensor (e.g., accelerometer, gyroscope, altimeter, etc.), audio sensor (e.g., microphone), or any other sensor. The sensor system can be used to implement fail-safes (e.g., activate alarm based on temperature sensor data and/or stimulus generator data), determine/trigger operational modes, or can be used for any other purpose.

The control module is preferably configured to implement one or more operation modes and/or apply one or more stimulation patterns to one or more electrodes, such as through one or more stimulus generators. The stimulation pattern preferably includes a current definition, wherein the current definition can include (or correspond to, be based on, etc.) any or all of a current amplitude (e.g., a static current amplitude (e.g., 1 milliampere (mA), 2 mA, less than 5 mA, etc.), a maximum current amplitude, a minimum current amplitude, etc.), a current waveform (e.g., sinusoidal, ramp, step, square, triangular, etc.), or any other current-related parameter. Additionally or alternatively, the stimulation pattern can include a voltage definition, power definition, heating command, or any other form of stimulus. The stimulation pattern can further include temporal parameters, such as, but not limited to: a duration of a stimulus pattern (e.g., 10 minutes of constant direct current stimulation, 20 minutes of on-off stimulation, etc.), a sequence of stimulation patterns (e.g., ramp-up followed by static hold), time of onset (e.g., apply a specified current definition at a specified time each day, upon detection of stimulation device placement on a user, etc.), a frequency of a current waveform, and/or a speed of propagation of a current definition. In some variations, the temporal parameters are determined using a timing subsystem including a set of timers. In some variations, a stimulation pattern or a set of stimulation patterns can be applied which dynamically propagate among and/or alternate between multiple electrodes. In one variation, each of a set of electrodes can be independently controlled by the control module. This can be implemented through a separate control module for each electrode, a single control module having separate ports for electrode, or any other combination or configuration of single or multiple control modules.

The control module can operate in operation modes, each of which preferably includes a current definition and a temporal parameter. Additionally or alternatively, the operation modes can include an on/off state, any form of stimulation pattern, only one of a current definition and a temporal parameter, or any other feature of electrode stimulation. Operation modes can be assigned and/or activated by a user (e.g., user makes selection through application on user device, sensor system of neurostimulation device detects a user voice command, user presses button on a control panel of the flexible backing, etc.), based on sensor data (e.g., pressure sensor detects when device has been placed on user), based on learned behavior of user (e.g., based on machine learning of user preferences and patterns), based on operation context (e.g., determined based on on-board sensor signals, remote device signals, etc.), or based on any other input. The operation modes of the control module preferably at least include a first operation mode corresponding to a stimulated electrode (e.g., 1 mA direct current applied to electrode) and a second operation mode corresponding to an unstimulated electrode (e.g., no current applied to electrode). In one example of this, for instance, the first operation mode prescribes a current definition (e.g., pulsing direct current) and the second operation mode prescribes no current definition. The first operation mode of the control module can further include any number of stimulation operation modes, wherein each of the stimulation operation modes prescribes a current definition and/or a temporal parameter. In one variation, for instance, there can be a set of operation modes each corresponding to different current values/amplitudes (e.g., 1 mA, 2 mA, 3 mA, etc.), different temporal parameters (e.g., current stimulation applied constantly for 20 minutes, current stimulation applied until turned off by a user, current stimulation pulsed for 1-ms durations spaced 1-ms apart, etc.). Additionally or alternatively, the control module can include any additional operation modes, a single operation mode, or any other operation mode.

3.3 System: Electrode Usage Module 130

The system 100 includes an electrode usage module 130, which functions to determine a usage associated with the electrode assembly (e.g., each of the electrode units, a single electrode unit, the collective set of electrode units, etc.). Additionally, the electrode usage module can function to monitor, track, record, and/or otherwise determine and use electrode usage information, determine usage of another component of the system 100, determine source information (e.g., manufacturer, batch number, etc.) associated with any or all of the electrodes, and/or perform any other suitable function.

Electrode usage can be defined by any number of usage parameters, alone or in combination, such as any or all of: temporal parameters, stimulation parameters, user-specific parameters (e.g., user preferences, user skin characteristics, etc.), and/or any other suitable parameters.

Temporal parameters associated with electrode usage can include any or all of: a duration of electrical stimulation (e.g., in seconds, minutes, hours, etc.) applied by one or more electrodes; a number of uses of one or more electrodes (e.g., in number of stimulation sessions, in number of full stimulation session, in number of partial stimulation sessions, etc.), a time since a first use of one or more electrodes (e.g., number of days, time since first used, time since first opened, time since manufactured, etc.), a frequency of electrode usage (e.g., average frequency, number of times per week, number of stimulation sessions per day, etc.), and/or any other suitable parameters.

Stimulation parameters associated with electrode usage can include any or all of: an amount of charge (e.g., total charge, average charge, etc.) delivered by one or more electrodes, an amount (e.g., amplitude, average amplitude, etc.) of current received and/or delivered by one or more electrodes, an amount of voltage established by one or more electrodes and a power source of the system 100, a power received at the set of electrodes from a power source of the system, a type of stimulation applied by one or more electrodes (e.g., tDCS, tACS, tRNS, etc.), a stimulation category (e.g., athletic performance, music performance, concentration, focus, memory, etc.), and/or any other suitable parameters.

User-specific parameters associated with electrode usage can include any or all of: a stimulation goal (e.g., athletic improvement, memory improvement, focus improvement, etc.), a user schedule (e.g., electrode purchasing schedule, stimulation schedule, user availability for replenishing electrodes, user travel schedule, etc.), a user preference on when electrodes should be replaced (e.g., when a diminished stimulation experience occurs, etc.), a set of user commands associated with stimulation (e.g., user's adjustment of intensity, user stimulation level selection, etc.), and/or any other suitable parameters.

Any or all of the usage parameters can function in enabling (e.g., through notifying a user) maintenance and/or replacement of electrodes. The maintenance and/or replacement can be recommended, for instance, based on any or all of: a duration of time since an electrode was manufactured, a duration of time since an electrode was first used, a number of stimulation sessions applied through an electrode, an effectiveness of an electrode (e.g., as indicated by the user), a wear and tear of the electrode (e.g., as indicated by the user, as indicated in an image, etc.), a number of uses of an electrode, a duration of use of an electrode, an amount of charge delivered through an electrode (e.g., amount of charge delivered per unit time), and/or any other suitable trigger(s).

The usage parameter(s) can be calculated at any or all of: an onboard computing subsystem (e.g., within a headset apparatus), a remote computing subsystem (e.g., cloud computing subsystem), a computing subsystem associated with a user device and/or a client application executing on the user device, any combination of computing subsystems, and/or any other computing subsystem.

The electrode usage module preferably includes a set of one or more tags for usage tracking, wherein the tags for usage tracking function to record the values of one or more usage parameters. Additionally or alternatively, the set of one or more tags can function to store information associated with the system 100 (e.g., manufacturer information) and/or user, detect a proper connection between a set of removable electrodes and a head apparatus, detect a proper contact between the set of electrodes and a skin surface of the user, guide a user in properly orienting one or more electrodes, and/or performing any other suitable function.

The set of tags are preferably serialized (e.g., individually serialized, serialized by lot, serialized by an intended system and/or headset apparatus model, serialized by the specific system, serialized by use case, serialized by application, etc.), which can be used in determining one or more usage parameters, triggering a change in stimulation (e.g., terminating stimulation, changing a parameter of a stimulation pattern applied to the user, etc.), triggering a purchase of refill electrodes (e.g., for the appropriate system model, based on the user preferences, etc.), allowing or disallowing use of the electrode(s) (e.g., based on serial number's presence on a whitelist vs. a blacklist), and/or for any other suitable use(s).

The set of tags preferably includes one or more passive tags (e.g., near field communication [NFC] tags), wherein one or more of the passive tags draws power (e.g., through magnetic induction) from a separate component of the system 100 (e.g., a power source arranged in a head apparatus component). The set of passive tags preferably communicates at a short-range distance, enabled by a close coupling between one or more of the set of passive tags (e.g., associated with the set of electrodes) and a communication sub-system such as an antenna connected to an embedded system (e.g., as part of a head apparatus of the system). Additionally or alternatively, the set of tags can include one or more active tags (e.g., a powered RFID chip or data storage device using a communication protocol such as a single-wire protocol), a magnetic tag, and/or any other suitable tags.

The set of tags can be locked (e.g., permanently locked, temporarily locked, selectively locked, etc.), unlocked, encrypted, unencrypted, and/or configured in any other suitable way. Additionally or alternatively, the set of tags can be written to a single time, multiple times, or any combination of both.

The set of tags is preferably configured to determine and/or verify an electrode type being mated with another component (e.g., headset apparatus) of the system, wherein an electrode type can include any or all of: one or more stimulation capabilities of the electrode, a size of the electrode, a shape of the electrode, and/or any other suitable features associated with the electrode. The set of tags is further preferably configured to determine one or more parameters associated with electrode coupling, such as any or all of: an alignment of the set of electrodes, an orientation of the set of electrodes, an area of contact of each of the set of electrodes with the user (e.g., to prevent too much stimulation from being delivered if only a partial area of the electrode is in contact with the user), and/or any other suitable coupling features. The set of tags is further preferably configured to determine and/or verify an intended device being paired with the set of electrodes, which can include any or all of: verifying a particular device model (e.g., headphone system versus a flexible electrode system for a forehead region), a particular user being or about to be stimulated (e.g., user who owns the particular device, user prescribed the particular electrode(s), a user registered for receiving stimulation, etc.), and/or any other suitable features of an intended device. The set of tags is further preferably configured to verify a manufacturer and/or batch information associated with the set of electrodes, which can function to: prevent a counterfeit electrode from being used to apply electrical stimulation, prevent electrodes which have been recalled from applying electrical stimulation to a user, prevent expired electrodes from applying electrical stimulation to a user, and/or be otherwise configured. Additionally or alternatively, the set of tags can be otherwise configured.

The set of tags is preferably arranged in the electrode assembly (e.g., in the electrode housing, in each of a set of electrode housings, etc.) and one or more receivers of the set of tags is arranged in another component (e.g., headset apparatus) of the system. Additionally or alternatively, the set of tags can be arranged and the tag receivers can be arranged in any other suitable way.

The set of tags preferably includes, implements, or stores a set of counters, which functions to determine and optionally record and/or store one or more temporal usage parameters, such as an amount of electrical stimulation applied to the user, which can include any or all of: a number of applied stimulation sessions applied, a duration of electrical stimulation applied (e.g., during a single electrical stimulation session, during multiple electrical stimulation sessions, etc.), and/or any other suitable parameters. The set of counters are preferably configured with one or more types of redundancy. This can function to ensure that an accurate electrode usage is calculated, enable unpowered tags (e.g., NFC tags, for minimized costs, etc.) to be used (since unsuccessful tag write(s) can commonly occur and thereby affect the accuracy of the tag results), and/or perform any other suitable function. In variations of counters configured for redundancy, the set of counters includes two sub-counters for each counter. Additionally or alternatively, the set of counters can include multiple counter types (e.g., a counter for stimulation session number and a counter for number of predetermined time periods). Additionally or alternatively, the set of counters can include any number of counters, with optional redundancy within each counter.

The set of tags can be configured to store immutable data, such as any or all of: tag formation data, hardware revision data, product type and ID, manufacturing location (and year, month, day of manufacture), serial number (e.g., to check for counterfeit electrodes), a CRC value (e.g., CRC-32) calculated based on the tag information (e.g., immutable tag information), and/or any other suitable information.

The set of tags can additionally or alternatively be configured to store mutable data, such as any or all of: a running count of stimulation sessions, a running count of time periods during which stimulation is applied, a CRC value (e.g., CRC-8) calculated based on the tag information (e.g., mutable tag information), and/or any other suitable information.

Figure 6A:
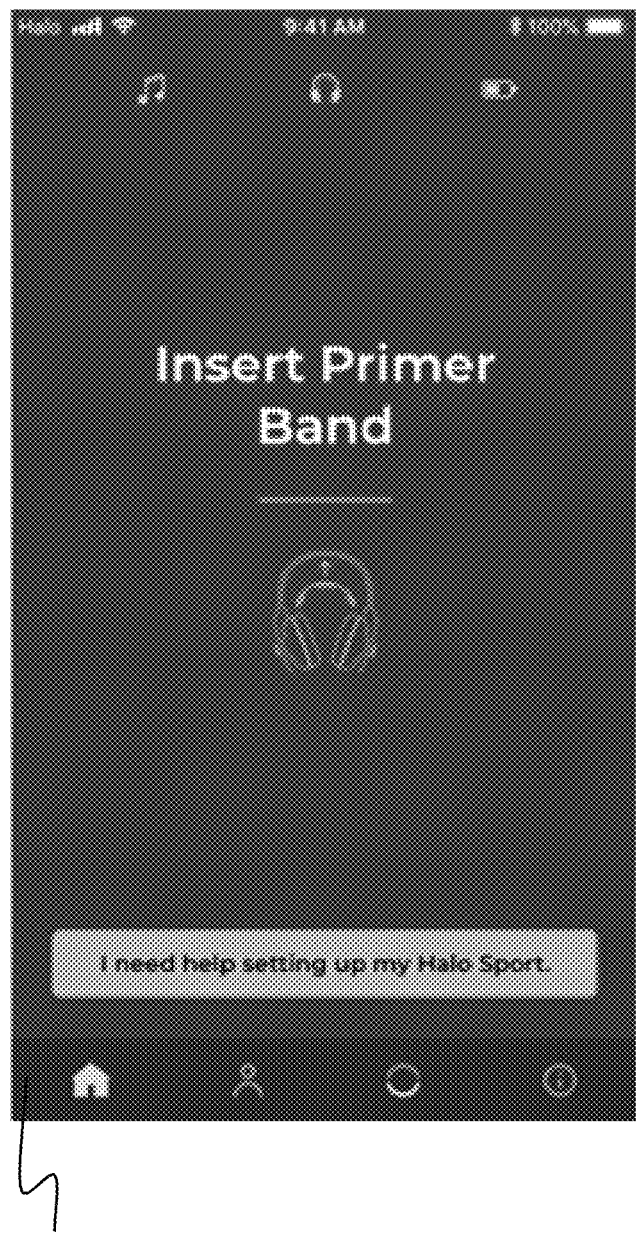
FIGS. 6A-6C depict a variation of a client application of the system.
Figure 6B:
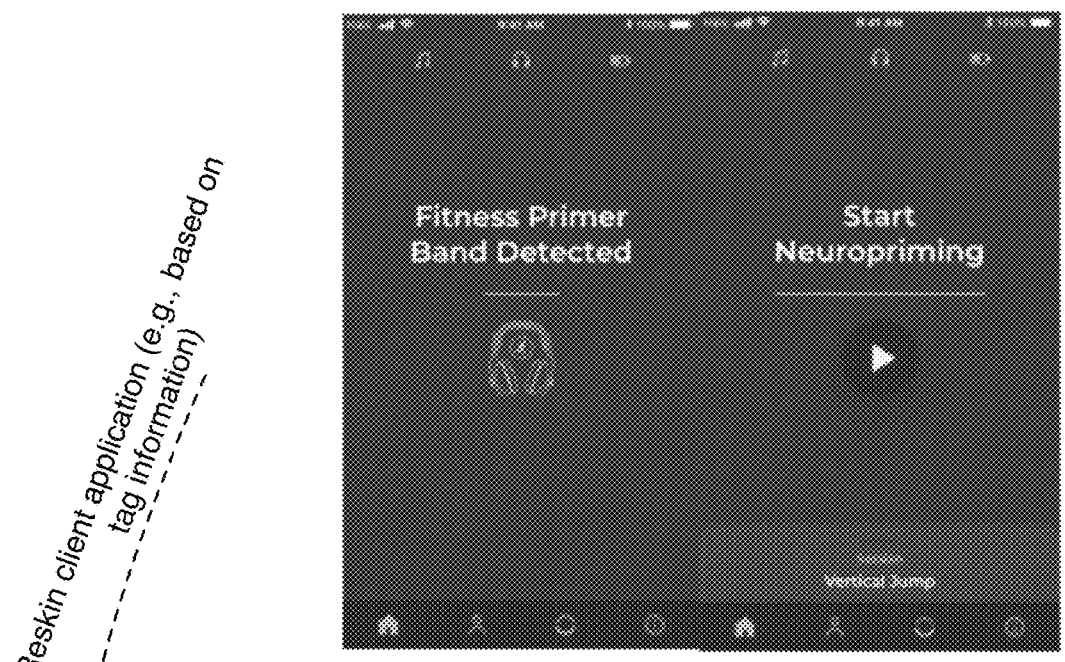
Figure 6C:
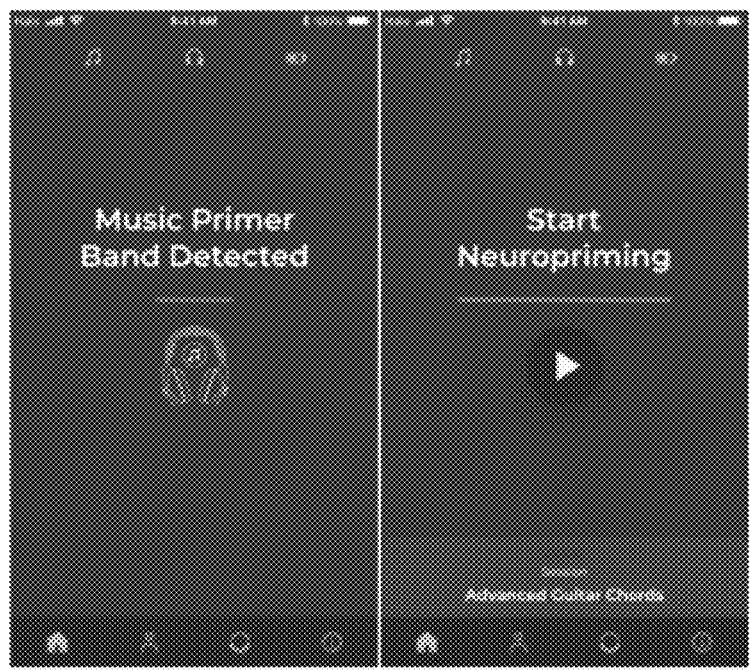

The set of counters are preferably configured to communicate with a client application (e.g., as shown in FIGS. 6A-6C) executing on a user device, wherein the client application is configured to read the count(s) from the set of counters and determine an assessment of electrode usage. Additionally or alternatively, any other computing subsystem(s) (e.g., onboard, remote, etc.) can be used in the assessment.

An electrode usage can be determined based on one or more usage parameters and any or all of: a set of equations and/or algorithms (e.g., stored at a client application and/or a user device executing the client application, stored onboard the headset apparatus, remotely arranged, etc.), a lookup table, a set of models, a set of thresholds, and/or any other suitable tools. Additionally or alternatively, electrode usage can be equal to the a usage parameter (e.g., number of counts) and/or determined based on any or all of: manufacturer information, user information, and/or any other information.

Based on the electrode usage value, one or more actions can be triggered (e.g., in response to the electrode usage being determined, immediately, after a predetermined time has passed, based on the value of the electrode usage, etc.), such as any or all of: sending a notification to a user (e.g., at the client application, at the user device, at the system 100, at a headset apparatus of the system 100, etc.), preventing stimulation, allowing stimulation, automatically placing an order for a replacement set of electrodes (e.g., from an e-commerce site, from a manufacturer of the system 100, etc.), initiating a change to a stimulation pattern (e.g., decreasing an amplitude of stimulation, decreasing a duration of stimulation, selecting a new stimulation pattern, etc.), adjusting a stimulation session (e.g., terminating a stimulation session), initiating a change to the client application (e.g., reskinning the client application, adjusting a user goal, etc.), rebooting the client application, and/or triggering any other suitable action.

In preferred variations, the set of tags includes a set of NFC tags (e.g., Type 1 NFC tag, Type 2 NFC tag, Type 3 NFC tag, Type 4 NFC tag, etc.). One or more of the set of tags is serialized, wherein the serial number indicates at least the system model (e.g., headphone device versus forehead device) and optionally the particular individual device. The serial number(s) are preferably able to compared with one or more whitelist(s) (e.g., of authentic electrode assemblies) and/or one or more blacklist(s) (e.g., of electrode assemblies used by counterfeiters), such that stimulation patterns can only be applied through electrodes associated with whitelisted systems, or such that stimulation patterns can be disallowed through electrodes suspected of being counterfeit.

In a first variation, as shown in FIGS. 3A-3H, the usage module includes a tag (e.g., an NFC tag) arranged in a cavity of an electrode assembly housing, wherein the electrode assembly housing forms a curved surface configured to apply electrical stimulation to a forehead of a user, and a tag receiver arranged in a housing of the head apparatus, wherein the head apparatus is removably couplable with the electrode assembly (e.g., through a set of conductive polymer contacts).

Figure 4:
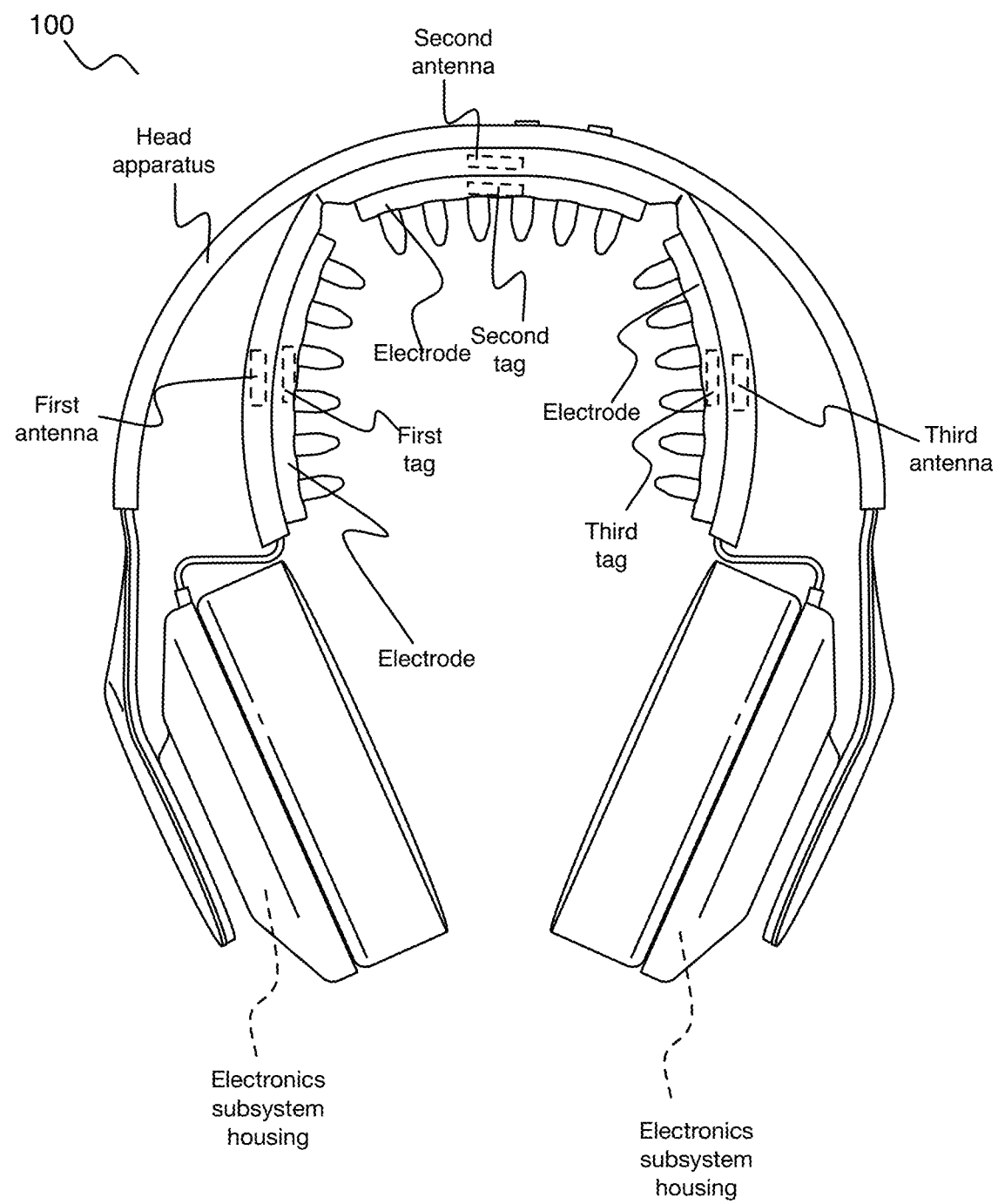
FIG. 4 depicts a variation of the system.

In a second variation, as shown in FIG. 4, the usage module includes a tag (e.g., an NFC tag) arranged in one or more electrodes of a set of multiple electrodes, wherein each of the set of electrodes is removably couplable (e.g., has its own electrode housing with connector(s)) with a head apparatus configured to be worn as a headset. In a first example, each electrode has its own tag, and the headset apparatus has a corresponding receiver for each tag. In a second example, each electrode has its own tag, and the headset apparatus has a single receiver for the tags. In a third example, the system includes a single tag (e.g., at the middle electrode) and a single receiver.

Figure 5:
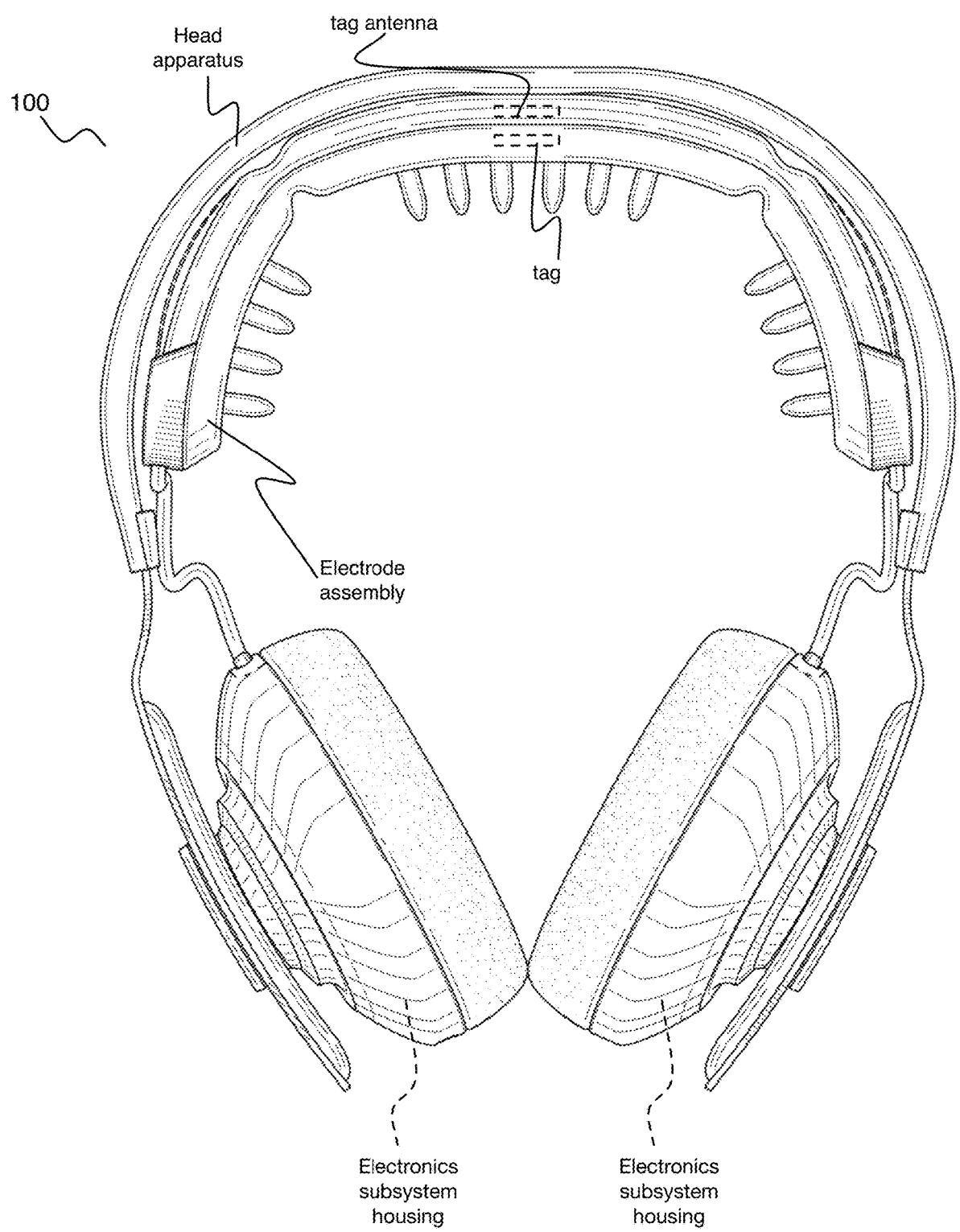
FIG. 5 depicts a variation of the system.

In a third variation, as shown in FIG. 5, the usage module includes a tag (e.g., an NFC tag) arranged in a single electrode housing connecting a set of multiple electrodes together, wherein the electrode assembly is removably couplable from a head apparatus configured to be worn as a headset and defining a cavity configured to include a tag receiver.

3.4 System: Communication Module 140

The system 100 preferably includes a communication module 140 configured to establish wireless communication between the control module and a user device (e.g., as described below). Additionally or alternatively, the communication module can be configured to establish communication between the electrode usage module and a user device, establish wired communication between any system components, and/or establish communication between any components of the system 100.

The communication module can include any number of communication components, such as any or all of: an antenna, WiFi chip, Bluetooth chip, a radio-frequency identification (RFID) system (e.g., RFID tag, RFID chip, etc.), and/or any other component(s).

3.5 System: Stimulus Generator 150

The system 100 includes a stimulus generator 150 (e.g., stimulus deliverer, current deliverer, current stimulus deliverer, etc.), which functions to transmit an electrical stimulus (e.g., based on an operation mode) to one or more electrodes of the electrode assembly and/or to operate in one or more operation modes. Additionally or alternatively, the stimulus generator can function to apply other stimuli, such as, but not limited to: a magnetic stimulus, ultraviolet (UV) light, heat, water, and/or any other stimuli. The stimulus generator is preferably electrically coupled to one or more electrodes (e.g., to the conductive layer(s) of a layered electrode, the hydrophilic layer(s) of a layered electrode, etc.), a control module, and a power module of the system, but can additionally or alternatively be connected to a subset of these (e.g., when the control module is remote), connected to any other element of the system, wirelessly connected to any element within or outside the system, and/or mechanically connected to any element. The stimulus generator preferably comprises a current generator/current stimulus deliverer (e.g., that generates direct current, alternating current, both direct and alternating, etc.), but can additionally or alternatively include a voltage generator/voltage stimulus deliverer and/or any other suitable generator/stimulus deliverer configured to facilitate transmission of an electrical stimulus. As such, the stimulus generator can provide one or more current definitions, such as a direct current (DC), an alternating current (AC), an AC component superimposed on a DC component, a monophasic pulsatile waveform, a symmetrical biphasic pulsatile waveform, an asymmetrical biphasic pulsatile waveform, and any other suitable stimulation profile. The waveform produced by the stimulus generator preferably can be described by parameters comprising amplitude and duration, but additionally or alternatively comprising any other suitable parameter(s), such as modulation frequency, step size, mean amplitude, or root mean squared (RMS) value. Furthermore, any one or more of the above parameters can be configured to be modulated by the stimulus generator, such that the stimulus generator can produce any one or more of: modulated amplitudes, modulated frequencies, and modulated pulse durations (e.g., modulated parameters characterized by exponential decay, exponential growth, or any other suitable growth or decay profiles). While one stimulus generator is described, an electronics subsystem can, in some variations, comprise more than one stimulus generator (e.g., a separate stimulus generator for each electrode), where the control module is configured to multiplex output of the additional stimulus generators to one or more electrodes or subsections thereof.

3.6 System: Sensor Subsystem 160

The system 100 can additionally or alternatively incorporate or cooperate with a sensor subsystem 160 including one or more of: biological sensors (e.g., EEG sensors, ECG sensors, etc.), transducers (e.g., optical sensors, optical emitters, ultrasonic transducers, etc.), additional sensors (e.g., temperature sensors, activity detecting sensors, sensors associated with position, velocity, or acceleration detection, biometric sensors, etc.) for sensing signals from the user, additional sensors (e.g., temperature sensors, barometric pressure sensors, light sensors, microphones, etc.) for sensing signals from the environment of the user, and any other suitable module. The sensors can be incorporated into any or all of: the headset apparatus and/or any other component(s) configured to be coupled to a user (e.g., the electrode assembly), the user device, and/or any other device.

3.7 System: Electrical Coupling Subsystem 170

The system 100 includes an electrical coupling subsystem 170 (e.g., coupler assembly, electrical coupler, conductive frame, set of electrical cables, etc.), which functions to electrically connect the electrode assembly with the control module. Additionally or alternatively, the electrical coupling subsystem can function to mechanically connect the electrode assembly with the control module, connect (e.g., electrically connect, mechanically connect, etc.) the electrode assembly with other components of the system 100, and/or perform any other suitable function.

In one variation, the electrical coupling subsystem 170 includes a conductive polymer frame configured to connect each of the electrodes to the control module.

3.8 System: User Device 180 and Client Application 190

The system 100 can include and/or be configured to interface with a user device 180, wherein the user device 180 functions to execute one or more client applications 190. Additionally or alternatively, the user device 180 can function to perform part or all of the processing of the system, receive and/or store data from the system (e.g., from the usage module), provide an interface with a remote computing subsystem and/or remote storage, and/or perform any other suitable function.

The user device is preferably separate and distinct from the electrode assembly and head apparatus, but can additionally or alternatively be integrated with one of these components or otherwise arranged. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi transceiver(s), Bluetooth transceiver(s), cellular transceiver(s), etc.), or any other suitable component.

The client application 190 functions to provide an interface with the user (e.g., to receive user inputs, to provide outputs to a user, etc.). Additionally or alternatively, the client application 190 can function to process any or all of the data (e.g., number of counts, data received at tag, etc.) received at the system 100, store data (e.g., predetermined stimulation sessions to be applied through the electrode assembly, usage data, number of counts, calculation based on number of counts, cyclic redundancy check calculation, etc.), retrieve data (e.g., from a lookup table at a remote computing system), provide information and/or stimulation options to a user (e.g., type of stimulation, task options, stimulation session options, stimulation session parameters, etc.), and/or perform any other suitable function.

The client application can optionally be reskinned based on one or more parameters (e.g., electrode type, headset type receiving the electrode assembly, electrode usage, electrode condition, etc.) associated with the set of electrodes. In a first variation, for instance, the client application can reskin based on an electrode type identifier (e.g., serial number) received from the tag associated with the electrode assembly. In a specific example, the client application reskins as an application for musicians upon detection of a tag indicating an electrode assembly intended for use in acceleration of fine motor training. In a second specific example, the client application reskins as an application for athletes upon detection of a tag indicating an electrode assembly intended for use in acceleration of strength and explosiveness training. Additionally or alternatively, the client application can be reskinned based on user input (e.g., desired task, survey, etc.), a user schedule, environmental information (e.g., location), and/or any other suitable parameters.

The client application can optionally check for an electrode assembly being present before initiating and/or continuing with an already initiated electrical stimulation session. Additionally or alternatively, an orientation of the electrode assembly can be checked, a number of electrodes can be checked, a position and/or location of the electrodes can be checked, this can be not checked, any information can be checked at a processing subsystem onboard the head apparatus, and/or any other suitable information can be checked at any suitable component(s) of the system.

The client application can optionally visually guide the user (e.g., by indicating on a graphic display of the user device) in properly placing a set of electrodes (e.g., upon determining that the electrodes have been placed incorrectly, any time the user is coupling electrodes to a head apparatus, etc.), guide the user through audio (e.g., telling the user that the electrodes are not properly placed, telling the user how to adjust placement for proper use, etc.), and/or otherwise assist the user in properly coupling a set of electrodes with a head apparatus.

In some variations, the usage module reports to a back-end database associated with the client application and/or user device, which logs or tallies usage of the electrode assembly (e.g., number of counts).

In additional or alternative variations, the client application is configured to compute one or more calculations (e.g., a cyclic redundancy check calculation) based on the usage data, which functions prevent data corruption and/or account for an improper data write on a tag of the usage module. In a specific example, a cyclic redundancy check (CRC) calculation is made at the client application (e.g., via a processing subsystem of the user device), which is compared with a calculated CRC value stored at the tag when a count value is transmitted from the tag to the client application (e.g., via the communication module of the head apparatus).

3.9 System: Head Apparatus

The system can include a head apparatus, which functions to position the set of electrodes at a head region (e.g., forehead, motor cortex region, etc.) of the user. The head apparatus includes a housing, which defines a set of one or more cavities. The set of cavities preferably includes at least part of a control module 120, at least part of an electrode usage module 130 (e.g., a tag receiver), a communication module 140, and a stimulus generator. Additionally or alternatively, any or all of a power source, sensor subsystem 160, electrical coupling subsystem 170, and/or any other suitable components can be arranged within a cavity of the head apparatus housing, attached to the head apparatus housing, and/or otherwise coupled to the head apparatus.

The head apparatus can additionally define and/or include any number of optional components, such as any or all of: an attachment mechanism (e.g., headband, strap, etc.), a set of ear pads, speakers, buttons, and/or any other suitable features.

In preferred variations, the head apparatus includes one or more of the head apparatuses described in any or all of: U.S. patent application Ser. No. 14/470,683, filed 27 Aug. 2014, now issued as U.S. Pat. No. 9,889,290, U.S. patent application Ser. No. 14/878,647, filed 8 Oct. 2015, now issued as U.S. Pat. No. 9,486,618, U.S. patent application Ser. No.

15/335,240, filed 26 Oct. 2016, now issued as U.S. Pat. No. 10,315,026, U.S. patent application Ser. No. 15/916,170, filed 8 Mar. 2018, each of which is incorporated in its entirety by this reference. Additionally or alternatively, any other suitable head apparatus can be used.

3.10 System: Variations

In a first variation of the system (e.g., as shown in FIGS. 3A-3H), the system includes an electrode assembly including a set of multiple electrodes configured to be arranged at a head region of the user; an electrode assembly housing configured to support and position the electrodes, wherein the electrode assembly has a curved shape to conform to the forehead of the user; a usage module including an NFC tag arranged in a cavity defined the electrode assembly housing, wherein the NFC tag stores immutable data, mutable data, and includes a set of counters configured to record a number of stimulation sessions applied to the headset as well as a duration of time during which stimulation is applied, and an NFC tag receiver arranged in an internal cavity defined by the head apparatus housing, which mimics the curvature of the electrode assembly housing, and is configured to connect and disconnect with the electrode assembly housing through a set of conductive polymer contacts; a strap; and a client application configured to execute on a user device, wherein the client application receives information from the tag via a communication module onboard the head apparatus.

Figure 7:
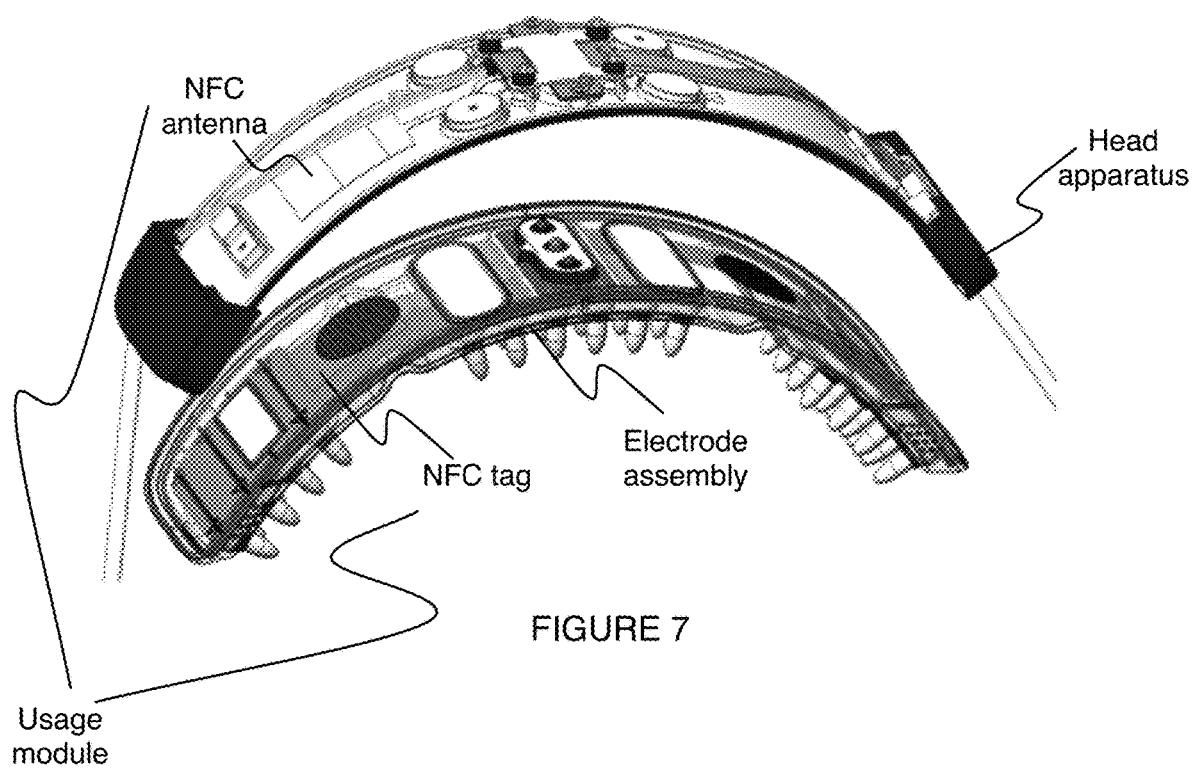
FIG. 7 depicts a variation of an electrode usage module.

In a second variation of the system (e.g., as shown in FIG. 4, as shown in FIG. 5), the system includes an electrode assembly including a set of multiple electrodes configured to be arranged at a head region of the user; an electrode assembly housing configured to support and position the electrodes, wherein the electrode assembly has a curved shape to conform to motor cortex head region (e.g., top of the head) of the user; a usage module (e.g., as shown in FIG. 7) including at least one NFC tag arranged in a cavity defined the electrode assembly housing, wherein the NFC tag stores immutable data, mutable data, and includes a set of counters configured to record a number of stimulation sessions applied to the headset as well as a duration of time during which stimulation is applied, and an NFC tag receiver arranged in an internal cavity defined by the head apparatus housing, which mimics the curvature of the electrode assembly housing, and is configured to connect and disconnect with the electrode assembly housing through a set of conductive polymer contacts; a headset including a set of ear pads; and a client application configured to execute on a user device, wherein the client application receives information from the tag via a communication module onboard the head apparatus.

4. Method 200

As shown in FIG. 2, a method 200 for electrically stimulating a user includes: reading a tag of the electrode assembly S210. Additionally, the method 200 can include any or all of: determining and/or updating an electrode usage S230; and triggering an action based on the tag S240; applying electrical stimulation to a user S220; refraining from applying electrical stimulation to a user S218; coupling an electrode assembly with a head apparatus S205; receiving an input from a user to initiate an electrical stimulation session; transmitting tag information S215; updating the tag; verifying tag information; and/or any other suitable process(es). Further additionally or alternatively, the method 200 can include any or all of the processes described in any or all of: U.S. patent application Ser. No. 14/470,747, filed 27 Aug. 2014, now issued as U.S. Pat. No. 9,630,005, U.S. application Ser. No. 15/426,212, now issued as U.S. Pat. No. 10,315,033, U.S. patent application Ser. No. 15/059,095, now issued as U.S. Pat. No. 9,782,585, U.S. patent application Ser. No. 16/195,728, filed 19 Nov. 2018, and any of the Patent Applications and/or Issued Patents described above, each of which is incorporated in its entirety by this reference.

The method 200 functions to determine a usage (e.g., number of stimulation sessions and duration of stimulation session) associated with one or more electrodes of a system for providing electrical stimulation to a user (e.g., to a head region of a user). Additionally or alternatively, the method 200 can function to prevent stimulation, allow stimulation, verify an electrode of a system (e.g., compare with a set of whitelisted electrodes, compare with a set of blacklisted electrodes, etc.), ensure a safety of one or more electrodes (e.g., verify an orientation of the electrode(s), verify an alignment of the electrode(s), ensure proper contact with a user, ensure stimulation delivery is through at least a majority of the surface area of the electrodes, etc.), ensure that a user has a sufficient supply of electrodes (e.g., by auto purchasing electrodes through an e-commerce site, by notifying a user that their electrodes need to be replaced soon, etc.), by adjusting a client application used with the electrodes (e.g., reskinning the application based on the detected electrode type), adjusting a stimulation session (e.g., terminating the stimulation session, adjusting an amplitude of current delivered in the stimulation session, etc.), and/or performing any other suitable function.

The method 200 is preferably performed with a system 100 as described above. Additionally or alternatively, any or all of the method 200 can be performed with any other suitable system(s).

4.1 Method: Coupling an Electrode Assembly with a Head Apparatus S205

The method 200 can include coupling an electrode assembly with a head apparatus S205, which functions to prepare the system for applying electrical stimulation to a user. Additionally, S205 can function to bring a tag (e.g., passive tag, NFC tag, etc.) of the electrode assembly within range of a tag reader (e.g., and power source) of the head apparatus.

S205 preferably includes establishing both a mechanical and electrical connection (e.g., through a set of conductive polymer contacts) between the electrode assembly and the head apparatus, but can additionally or alternatively establish any suitable connection or combination of connections.

4.2 Method: Reading a Tag of the Electrode Assembly S210

The method 200 includes reading a tag of the electrode assembly S210, which functions to determine information associated with the set of electrodes of the electrode assembly. As such, S210 can have any or all of the following additional functions: determining a system model associated with the electrode(s), determining a use case or goal associated with the set of electrodes (e.g., athletic improvement, music improvement, focus improvement, memory improvement, etc.), determining and/or adjusting a stimulation parameter of stimulation applied to the user, and/or performing any other suitable function.

The tag is preferably read by a tag reader (e.g., associated with a control module and a communication module), further preferably a tag reader arranged in a head apparatus of the system. S210 is preferably performed in response to S205, but can additionally or alternatively be performed prior to S205 (e.g., in response to a predetermined distance between the tag and the tag reader being met), after S205, multiple times throughout the method 200, and/or at any other suitable time(s).

S210 optionally includes comparing information read from the tag with a set of whitelists (e.g., stored remotely, stored in the cloud, stored in storage onboard the system, etc.) and/or a set of blacklists (e.g., stored remotely, stored in the cloud, etc.), which functions to verify that any or all of the electrodes in the electrode assembly are fit for use (e.g., not counterfeit). In some variations, this includes reading a serial number off of the tag and comparing with one or both of a whitelisted or blacklisted set of serial numbers. In the event that the serial number is associated with a counterfeit system, the method 200 can be terminated and/or the other electrodes prevented from delivering stimulation to the user.

S210 can additionally or alternatively include determining a system model (e.g., headband system, forehead system, athletic use system, focus improvement system, etc.) associated with the electrode assembly, such as reading a model serial number (e.g., different than the whitelist serial number described above, the same as the whitelist serial number described above, etc.) from the tag. The model serial number can be used to determine one or more stimulation patterns and/or stimulation pattern parameters (e.g., amount of charge to be delivered based on the size and number of electrodes associated with the system model, amplitude of current to apply, which stimulation waveform to apply, stimulation duration, stimulation session frequency, etc.) to apply to the user, configure a client application (e.g., reskin for athletic activities, reskin for focus activities, select an appropriate library of stimulation patterns to offer to the user, pull up user progress information and/or user preferences, etc.), automatically place an order and/or recommend that the user places an order for replacement electrodes of the appropriate type, and/or be used in any other suitable way. In some variations, the model serial number is read to determine which of a set of system models (e.g., headband form factor versus flexible forehead form factor) is associated with the received electrodes and optionally which types of stimulation patterns and their associated parameters (e.g., current amplitude, frequency, duration, etc.) should be applied.

S210 can further additionally or alternatively include reading one or more electrode usage parameters from the tag, which can function in any or all of the same ways as the model serial number and/or in any other suitable way. In some variations, the electrode usage is read and compared with a set of one or more thresholds to determine if the electrodes are suitable for use in applying stimulation. In the event that the usage of the electrodes meets or exceeds a predetermined threshold, or based on the result of any other comparison or determination, any or all of the remaining processes of the method 200 can be terminated (e.g., active electrical stimulation stopped) and/or prevented (e.g., preventing stimulation from being applied, refraining from applying electrical stimulation, etc.), a notification can be provided to the user, replacement electrodes can be ordered, and/or any other suitable outcome can be triggered. In some variations, additional or alternative to the previous variations, multiple thresholds can exist, wherein the triggered outcome depends on which threshold(s) are exceeded. In a specific example, a first usage threshold triggers a notification to the user (e.g., to purchase new electrodes, to re-wet the current electrodes in a conductive solution, etc.) while a second usage threshold prevents stimulation from being applied.

Further additionally or alternatively, any other information can be read from the tag.

4.3 Method: Transmitting Tag Information S215

The method can optionally include transmitting tag information S215, which can function to store the tag information, update remotely stored tag information, enable the tag information to be compared with remotely stored information (e.g., whitelists, blacklists, usage thresholds, etc.), be used in the calculation of other parameters (e.g., overall electrode usage, etc.), and/or be otherwise used.

The tag information can be transmitted to any or all of: a user device (e.g., storage of a user device), a client application executing on a user device, a remote computing subsystem (e.g., cloud storage), a back-end database, and/or any other location. The tag information is preferably transmitted wirelessly, but can additionally or alternatively be transmitted through a wired connection (e.g., in response to plugging the head apparatus into a user device).

S215 can be performed each time the tag is read, once an electrode usage parameter is determined, once one or more thresholds are met, prior to applying stimulation to a user, multiple times throughout a stimulation session (e.g., every time a counter is incremented), multiples times through the method 200, and/or at any other suitable time(s).

In one variation, S215 includes transmitting counter information to a client application executing on a user device communicatively coupled to the headset apparatus. In a specific example, the counter information is transmitted each time a stimulation session is completed. Additionally or alternatively, the counter information can be transmitted each time a stimulation session begins, in response to S205, each time a counter is incremented, when requested by the client application, based on a schedule (e.g., once per day, once per week, etc.), and/or at any other suitable time(s).

4.4 Method: Applying Electrical Stimulation to a User S220

The method 200 can include applying electrical stimulation to a user S220, which functions to improve a user's performance and/or mental state in relation to a goal of the user.

The electrical stimulation is preferably provided in accordance with a stimulation pattern (e.g., stored at the user device, stored at the client application, stored onboard the system at the control module, etc.), wherein the stimulation pattern (e.g., waveform) is defined by a set of stimulation parameters (e.g., current amplitude, current frequency, duration of stimulation, etc.). The stimulation parameters can be any or all of: predetermined, dynamically determined (e.g., based on the electrode usage, based on electrode tag information, etc.), user-specific, user-agnostic, and/or otherwise determined.

The electrical stimulation is preferably provided upon prompting by a user (e.g., at a client application, at a set of buttons on the head apparatus, etc.) and further preferably includes verifying that an electrode assembly has been coupled to the head apparatus (e.g., to prevent stimulation from being applied through bare contacts). Additionally or alternatively, S220 can include verifying that an electrode usage parameter (e.g., number of stimulation session counts, stimulation session total duration, etc.) is below a predetermined threshold, thereby ensuring that stimulation can be safely and effectively applied. Further additionally or alternatively, electrical stimulation can be provided according to a schedule, only available to a user once one or more criteria are satisfied (e.g., electrode assembly connected to the head apparatus, electrode usage below a predetermined threshold, etc.), and/or provided in response to any suitable trigger(s) and with any suitable check(s) (e.g., verifying that at least a predetermined surface area of the electrode is in contact with the user).

Additionally or alternatively, the method 200 can include refraining from applying electrical stimulation to a user S218. S218 preferably occurs prior to S220 and can optionally prevent S220 from occurring, such as in the event that it is determined from reading a tag of the electrode assembly S210 that a number of uses of the electrode assembly has exceeded a predetermined threshold. S218 can occur at any time during the method 200 (e.g., after S210, after S215, after S230, after updating the tag, during S240, etc.), multiple times throughout the method 200, and/or at any other suitable time(s). S218 can optionally prevent further processes of the method 200 from being performed; additionally or alternatively, S218 can allow any further processes of the method 200 to be performed.

In some variations, the electrical stimulation is provided as described in any or all of: U.S. patent application Ser. No. 14/470,747, filed 27 Aug. 2014, now issued as U.S. Pat. No. 9,630,005, U.S. application Ser. No. 15/426,212, now issued as U.S. Pat. No. 10,315,033, U.S. patent application Ser. No. 15/059,095, now issued as U.S. Pat. No. 9,782,585, U.S. patent application Ser. No. 16/195,728, filed 19 Nov. 2018, each of which is incorporated herein in its entirety by this reference.

In one variation, separate or additional to those described, the user selects a stimulation session at either a client application executing on a user device or at a button of the headset apparatus; the control module verifies that an electrode assembly is coupled with the head apparatus; and the stimulus generator provides the stimulation session. In a specific example, the electrode usage is determined and/or referenced prior to administering the electrical stimulation, wherein the stimulation is prevented from being delivered if the electrode usage exceeds a predetermined parameter. Additionally or alternatively, the stimulation is still applied, but the method includes (e.g., prior to administering the stimulation, while administering the stimulation, etc.) providing a notification to the user to replace the electrodes.

4.5 Method: Determining and/or Updating an Electrode Usage S230

The method 200 can include determining and/or updating an electrode usage S230, which functions to keep track of the usage of one or more electrodes of the system.

S230 can include determining any or all of: a set of one or more temporal usage parameters (e.g., as described above), a set of one or more stimulation usage parameters (e.g., as described above), a set of one or more user-specific usage parameters (e.g., as described above), and/or any other usage parameters. S230 can optionally include performing a set of one or more calculations to determine an electrode usage (e.g., based on one or more usage parameter(s), based on other information, based on tag information, based on information stored at a client application, etc.), referencing a lookup table to determine an electrode usage, and/or otherwise determining an electrode usage. Additionally or alternatively, an electrode usage can be determined directly from a usage parameter (e.g., equal to a count value).

The electrode usage is preferably at least partially determined based on one or more temporal usage parameters, wherein the temporal usage parameters can include any or all of: a number of stimulation sessions, a duration of each stimulation session, a total duration of stimulation applied to a user (e.g., collective duration, sum of individual session durations, etc.), a duration of time in which the system is in an "on" operation mode, and/or any other suitable temporal parameters.

In preferred variations, S230 includes determining and tracking a temporal usage of a set of electrodes through a set of counters of a tag of the system. For systems including multiple electrodes, the electrodes preferably share a common counter subsystem. Alternatively, each electrode can include its own counter subsystem (e.g., and be replaced individually).

The counter(s) can be incrementally updated based on any or all of: a new stimulation session being initiated, a stimulation session ending, a stimulation session being interrupted and/or terminated, the passing of a predetermined time period (e.g., 64 seconds, 60 second, etc.), the occurrence of coupling between the electrode assembly and the head apparatus, the application of stimulation having one or parameters (e.g., current amplitude, duration, etc.) above a predetermined threshold, the application of stimulation having one or more parameters below a predetermined threshold, and/or any other suitable trigger.

Each counter preferably includes a set of redundant sub-counters in which at least one of the sub-counters is updated (e.g., incremented by 1, incremented by 2, etc.) upon satisfaction of the counter trigger (e.g., number of stimulation sessions). The redundancy of each counter functions to ensure that the counter is accurately tracking electrode usage and that no data has been lost in transmission, which can occur, for instance, when using passive tags (e.g., NFC tags). Alternatively (e.g., in active tags), any or all of the counters can be configured without redundancy. In some variations, for instance, each counter includes a set of two values, offset from each other by 1. Upon satisfaction of the counter's trigger (e.g., the start of a new stimulation session), each counter can be incremented by 1, the smaller value can be incremented by 2 and the larger value incremented by 0, or the counter values can be otherwise updated.

S230 can optionally include verifying any or all of the counter values, which can function to ensure proper data transmission. In variations involving NFC tags, for instance, verifying the counter values can function to ensure a write of the NFC tag is successful. The counter values are preferably verified through one or more transmission calculation processes, further preferably one or more checksum processes (e.g., calculations, comparisons, etc.). In some variations, a checksum at the tag is compared with a calculated checksum value (e.g., calculated at a control module onboard the system, calculated at the client application, etc.) to ensure that they match. The verification process can occur each time a counter value is updated, sporadically, upon initiation by a user, according to a schedule, and/or at any other time(s).

The checksum preferably takes into account the order of the entries of the tag, and is preferably calculated with a cyclic redundancy check (CRC) algorithm (e.g., CRC-8, CRC-32, etc.). Additionally or alternatively, the checksum calculation process (e.g., for a checksum value, for a different transmission calculation, etc.) can include any or all of: a Fletcher's checksum, an Adler checksum (e.g., Adler-32), and/or any other suitable process. Further additionally or alternatively, the transmission calculation can include any processes which do not take order into account (e.g., to reduce compute cost), and/or any other suitable process(es).

In a specific example of S230, one or more values of a first counter are updated each time a new stimulation session is initiated. As the stimulation is being applied, one or more values of a second counter are updated each time that a predetermined period of time (e.g., 64 seconds, 60 seconds, etc.) passes during a stimulation session, thereby keeping track of the amount of time the associated electrode(s) are applying stimulation. A calculation can optionally be done (e.g., at a processor onboard the system, at a processor onboard a user device, at a remote processor, etc.) to determine the total time stimulation has been applied.

In another specific example of S230, redundancy is attained by updating at least one of the sub-counters but not all of the sub-counters, while including with each sub-counter a CRC or other checksum (e.g., a CRC-8) which protects only that sub-counter. In this example, in order to determine the true value of the counter, each sub-counter is read and the true value of the counter is assumed to be the highest sub-counter value having an intact checksum; at the next update point, a different sub-counter whose value was not the highest intact value is incremented (including update of the associated CRC-8). The procedure described in this example determines the true value of the counter with minimal error and minimal chance of additionally propagating errors, even in the presence of errors in writing or reading an individual sub-counter.

Additionally or alternatively, the electrode usage can be determined based on a total amount of charge delivered through one or more of the set of electrodes, a surface area through which charge is actually being delivered, a time since the electrode(s) were last replaced, and/or any other usage parameter(s).

In one variation, determining an electrode usage includes upon detecting the initiation and/or a planned initiation of an electrical stimulation session, incrementing one or more values of a first counter; and each time a predetermined time period (e.g., 64 second time period) passes (e.g., based on a clock onboard the head apparatus, based on a clock onboard the electrode assembly, based on a clock onboard a user device, etc.), incrementing one or more values of a second counter. The counter values can be used to calculate a CRC value, wherein the CRC value is compared with a CRC value calculated at the client application (e.g., each time data is transferred to the client application, when determining an electrode usage, etc.) to ensure that no data was lost in transmission.

4.6 Method: Triggering an Action Based on the Tag S240

The method 200 can include triggering an action based on the tag S240, which functions to enable the user to safely and effectively receive electrical stimulation. Additionally or alternatively, S240 can function to assist in troubleshooting a problem encountered by the system, assisting a user in having a constant supply of electrodes, tailoring a user experience via a client application, and/or performing any other function.

S240 is preferably performed after S230, further preferably in response to a determination that the electrode usage has reached and/or exceeded a determined electrode usage threshold. Additionally or alternatively, S240 can be performed based on any suitable information (e.g., other tag information such as electrode type) and/or at any or all of the following time(s): in response to S210 (e.g., based on other tag information), in response to S215 (e.g., based on other tag information received at a client application); in response to the user indicating a problem with the system (e.g., through feedback provided at a client application), in response to irregular behavior of a user when interacting with the system (e.g., large number of adjustments to stimulation, repeat switching between an "on" and an "off" operation mode, repeat number of complaints to customer service, etc.), upon prompting by a user, upon prompting by the system, multiple time(s) throughout the method, and/or at any other suitable time(s).

S240 can include triggering a notification to the user. The notification is preferably provided at a client application executing on a user device, but can additionally or alternatively be provided elsewhere at the user device (e.g., through an SMS text message), through a phone call, at another component of the system (e.g., at the head apparatus, through an LED indicator of the head apparatus, etc.), and/or through any other suitable interface at any suitable system component(s).

The content of the notification (e.g., message, alert, reminder, etc.) can optionally be determined based on the value of the electrode usage (e.g., a number of counts, a number of stimulation sessions applied to the user, a duration of time in which stimulation is applied to the user, etc.), wherein a severity of the notification increases as the electrode usage increases. In some variations, for instance, a first notification (e.g., notifying the user that the electrodes should be replaced soon, reminding the user to place an order to purchase replacement electrodes, recommending a different stimulation session to the user, etc.) is sent at a first time point based on a first electrode usage threshold, and second notification (e.g., notifying the user that replacement electrodes have been ordered, notifying the user that stimulation will not be applied, notifying the user that a different stimulation session has been selected, etc.) is sent at a second, later time point based on a second electrode usage threshold (e.g., higher than the first).

Additionally or alternatively, the content of the notification can be determined based on any other suitable information, such as other information of one or more tags. Further additionally or alternatively, the notifications can be consistent for any electrode usage, and/or be otherwise determined.

Any or all of the notifications can optionally prompt and/or require user input, such as any or all of: a user acknowledgement that electrode usage information has been received; a user desire to proceed with stimulation in light of electrode usage information; a user input to purchase replacement electrodes; a user acknowledgement that the notification has been received (e.g., and that the stimulation has been adjusted); and/or any other suitable input. Additionally or alternatively, the method can include receiving a read receipt, proceeding without prompting and/or requiring user input, and/or any other suitable process(es).

A notification can optionally prompt any or all of the other actions described below.

S240 can additionally or alternatively include initiating a purchase of a replacement set of electrodes. The purchase can be initiated and/or completed through any or all of: the client application, a separate application (e.g., e-commerce application), a website (e.g., e-commerce website), and/or any other suitable platform. The purchase can occur automatically (e.g., upon reaching an electrode usage threshold), with user input (e.g., user permission, user permission at the client application, etc.), without user input, according to a schedule (e.g., based on electrode usage, based on the purchase date of the electrodes, etc.), based on a purchase history of the user, and/or any other suitable time(s).

S240 can further additionally or alternatively include adjusting stimulation and/or otherwise altering a stimulation session. This can include adjusting one or more stimulation parameters of a stimulation session, such as any or all of: an amplitude (e.g., current amplitude, voltage amplitude, etc.), a frequency (e.g., frequency of stimulation occurrence, frequency of stimulation waveform, etc.), a charge delivered (e.g., total charge delivered during stimulation session, charge delivered per electrode, charge delivered per unit surface area, etc.), a power, a voltage (e.g., through a log voltage stepdown), a duration of stimulation, and/or any other suitable parameter(s). Additionally or alternatively, a stimulation session can be terminated or otherwise altered. Adjusting the stimulation can occur during the stimulation session, prior to administering a planned stimulation session, prior to administering a next stimulation session, and/or at any other time(s).

In one variation, S240 includes applying a voltage stepdown (e.g., a logarithmic stepdown, a proportional stepdown, a subtractive stepdown, etc.) upon determining that an electrode usage has exceeded a predetermined electrode usage threshold.

S240 can further additionally or alternatively include adjusting a client application and/or any suitable interface with the user (e.g., display onboard the head apparatus). The client application can be adjusted based on tag information, such as any or all of: electrode type, system model, electrode usage, user information, and/or any other suitable information. The adjustment can reflect any or all of the actions described above (e.g., adjusted stimulation parameters, notification, etc.), an updated user goal, and/or any other suitable information. In some variations, S240 includes selecting and/or reskinning the client application based on the electrode type and/or associated system model and use case. In a first specific example (e.g., as shown in FIG. 6C), an application can be reskinned as an application for musicians, for instance, upon detection of a tag indicating that the associated electrode assembly is intended for use in acceleration of fine motor training. In a second specific example (e.g., as shown in FIG. 6B), an application can be reskinned as an application for athletes upon detection of a tag indicating that the associated electrode assembly is intended for use in acceleration of strength and explosiveness training.

S240 can additionally or alternatively include initiating and/or assisting in one or more troubleshooting processes. If a user is encountering a problem with the system, for instance, electrode usage data can be assessed to see if the problem can be attributed to the electrodes. If the electrode usage is high, any or all of the above actions can be triggered, for instance, and if the electrode usage is low, a different action can be triggered, such as speaking with a customer service representative, recommending that the user send in the headset apparatus for repair, recommending that the user replace a different component of the system, and/or any other suitable action.

Additionally or alternatively, any other suitable action(s) can be triggered based on any suitable information.

4.7 Method: Variations

Figure 8:
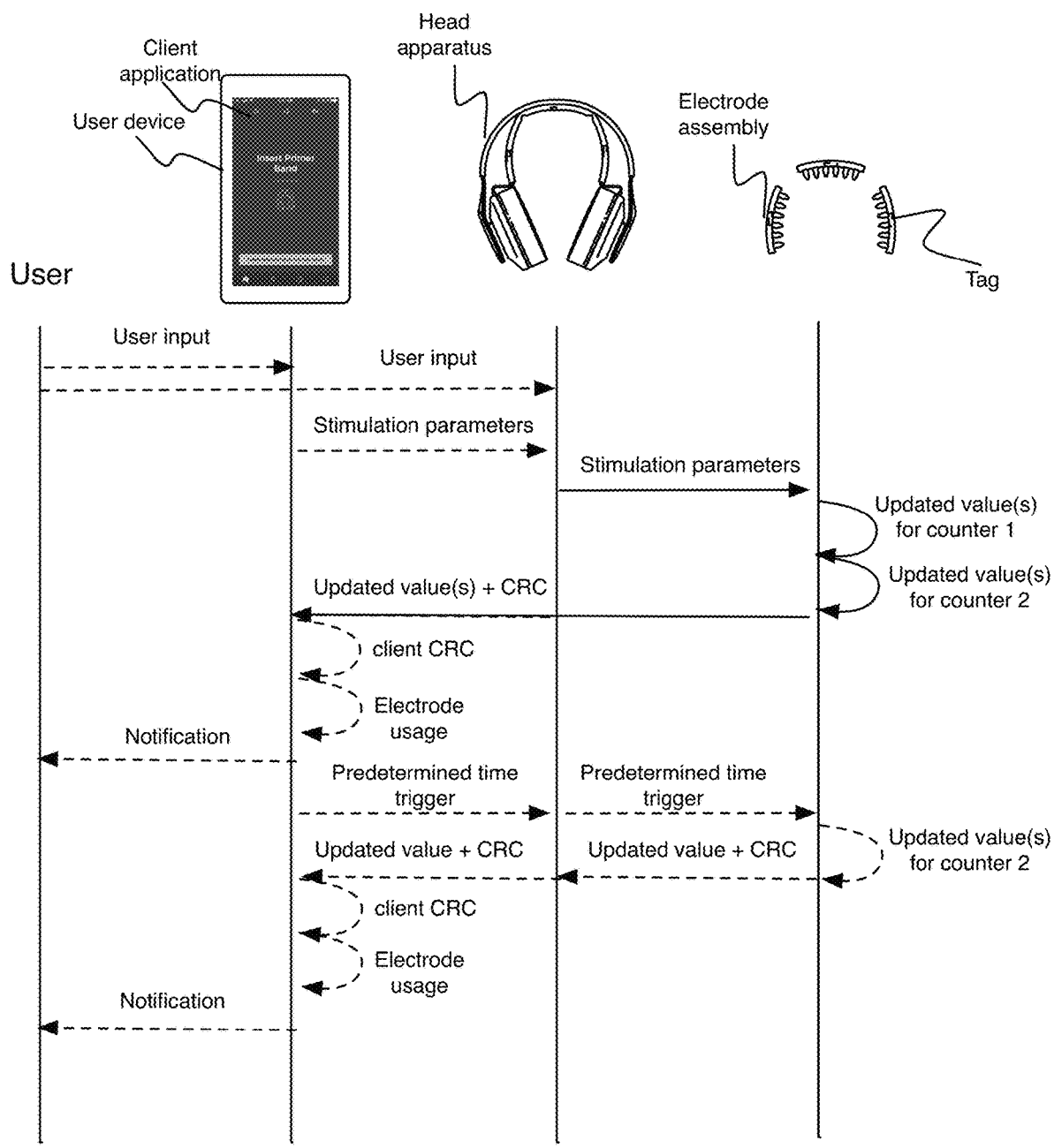
FIG. 8 depicts a variation of the method.

In a first variation (e.g., as shown in FIG. 8), the method 200 includes receiving user input at a client application; determining a set of stimulation parameters (e.g., at the client application, at the head apparatus, etc.) based on the user input; transmitting the stimulation parameters to the electrode assembly; at the electrode assembly, initiating and/or preparing to initiate a stimulation session in accordance with the stimulation parameters; updating one or more values of a first counter of a tag at the electrode assembly, wherein the first counter functions to track a number of applied stimulation sessions; updating one or more values of a second counter of a tag at the electrode assembly, wherein the second counter functions to track a number of predetermined time periods during which stimulation is being applied; transmitting the counter values and optionally a CRC value calculated based on the counter values to the client application; at the client application, calculated a CRC value to compare with the CRC value received from the tag (e.g., to ensure proper data transmission); determining an electrode usage based on these counter values (e.g., a total duration of stimulation, the counter values themselves, etc.); and upon determining that an electrode usage exceeds a predetermined threshold, notifying a user. Additionally or alternatively, the method 200 can include any other suitable processes.

The system 100 and method of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in a flowchart or block diagram may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals or neurostimulation will recognize from the previous detailed description and from the figures and claims, modifications and changes can be made to the preferred embodiments of the invention without departing from the scope of this invention defined in the following claims.

We claim:

1. A system for electrically stimulating a head region of a user, the system comprising:
   a head apparatus configured to be worn at the head region, the head apparatus comprising:
      a power source;
      a communication module; and
      a stimulus generator;
   wherein the power source, the communication module, and the stimulus generator are arranged in a first cavity, the first cavity defined by the head apparatus;
   an electrode assembly removably coupleable to the head apparatus, the electrode assembly comprising:
      a set of multiple electrodes; and
      an electrode support housing connecting the set of multiple electrodes and defining a second cavity;

an electrode usage module configured to track a usage of the electrode assembly, wherein the electrode usage module comprises:
  a near field communication (NFC) tag arranged in the second cavity, wherein the NFC tag comprises a counter subsystem comprising:
    a first counter configured to track a first counter value, the first counter value indicating an amount of stimulation applied by the electrode assembly, wherein the first counter comprises a set of multiple sub-counters for redundancy; and
    a second counter configured to track a second counter value, wherein the second counter comprises a second set of multiple sub-counters for redundancy;
  a receiver arranged in the first cavity, wherein the receiver is configured to receive information from the NFC tag;
a client application executing on a user device separate and distinct from the head apparatus, wherein the communication module is configured to communicatively connect the head apparatus and the user device, and wherein the client application receives the first counter value, further wherein the client application is configured to:
  verify the first counter value and the second counter value each time at least one of the first counter value and the second counter value is updated, wherein verifying the first counter value and the second counter value comprises comparing a set of checksum values stored at the NFC tag with a set of checksum values calculated at the client application; and
  determine an electrode usage parameter based at least partially on the first counter value and the second counter value.

2. The system of claim 1, wherein the NFC tag further comprises an identifier associated with a use case of the electrode assembly, wherein the client application is configured to be reskinned based on the identifier.

3. The system of claim 1, wherein in an event that the value of the electrode usage parameter exceeds a predetermined threshold, the client application prevents stimulation.

4. The system of claim 1, wherein the client application is configured to adjust a stimulation parameter of a stimulation session planned to be delivered by the stimulus generator to the user, wherein the stimulation parameter is adjusted based on the value of the electrode usage parameter.

5. The system of claim 4, wherein the stimulation parameter comprises a voltage, and wherein adjusting the stimulation parameter comprises implementing a voltage step-down in the event that the value exceeds a predetermined threshold.

6. The system of claim 1, wherein the electrode usage parameter comprises an amount of time that the electrode assembly is actively stimulating the user.

* * * * *